(12) United States Patent
Friedman

(10) Patent No.: US 11,786,561 B2
(45) Date of Patent: Oct. 17, 2023

(54) APPROACH TO SUSTAINED PRODUCTION AND DELIVERY OF NITRIC OXIDE AND S-NITROSOTHIOLS

(71) Applicant: Albert Einstein College of Medicine, Bronx, NY (US)

(72) Inventor: Joel M. Friedman, West Orange, NJ (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 17/933,224

(22) Filed: Sep. 19, 2022

(65) Prior Publication Data

US 2023/0064665 A1   Mar. 2, 2023

Related U.S. Application Data

(63) Continuation of application No. PCT/US2021/022734, filed on Mar. 17, 2021.

(60) Provisional application No. 62/991,861, filed on Mar. 19, 2020.

(51) Int. Cl.
| | | |
|---|---|---|
| *A61K 35/644* | (2015.01) | |
| *A61P 31/06* | (2006.01) | |
| *A61K 47/10* | (2017.01) | |

(52) U.S. Cl.
CPC ........... *A61K 35/644* (2013.01); *A61K 47/10* (2013.01); *A61P 31/06* (2018.01)

(58) Field of Classification Search
None
See application file for complete search history.

(56) References Cited

U.S. PATENT DOCUMENTS

| | | | |
|---|---|---|---|
| 11,484,493 | B2 | 11/2022 | Friedman |
| 2004/0054313 | A1 | 3/2004 | Molan |
| 2008/0057088 | A1 | 3/2008 | Blass et al. |
| 2009/0297634 | A1 | 12/2009 | Friedman et al. |
| 2012/0052095 | A1 | 3/2012 | Chaniyilparampu et al. |
| 2014/0017121 | A1 | 1/2014 | Schoenfisch et al. |
| 2014/0105986 | A1* | 4/2014 | Doxey ............... A61K 47/38 514/781 |
| 2015/0147396 | A1* | 5/2015 | Nacharaju ........... A61K 9/51 514/706 |
| 2017/0119814 | A1 | 5/2017 | Friedman et al. |
| 2018/0256509 | A1 | 9/2018 | Friedman et al. |
| 2022/0257642 | A1 | 8/2022 | Munro et al. |
| 2023/0069711 | A1 | 3/2023 | Friedman |
| 2023/0121214 | A1 | 4/2023 | Friedman |

FOREIGN PATENT DOCUMENTS

| | | | |
|---|---|---|---|
| WO | 2005/105059 | A1 | 11/2005 |
| WO | 2009/131931 | A1 | 10/2009 |
| WO | 2010/048724 | A1 | 5/2010 |
| WO | 2013/169538 | A1 | 11/2013 |
| WO | 2018/039752 | A1 | 3/2018 |
| WO | 2020/245574 | A1 | 12/2020 |

OTHER PUBLICATIONS

International Search Report and Written Opinion dated Dec. 12, 2022, in International Application No. PCT/US2022/075651, 16 pages.
Amalraj, A. et al. "A Novel Highly Bioavailable Curcumin Formulation Improves Symptoms and Diagnostic Indicators in Rheumatoid Arthritis Patients: A Randomized, Double-Blind, Placebo-Controlled, Two-Dose, Three-Arm, and Parallel-Group Study", J Med Food. Oct. 2017;20(10):1022-1030.
Anand, P. et al. "Curcumin and cancer: an "old-age" disease with an "age-old" solution", Cancer Lett. Aug. 18, 2008;267(1):133-164.
Babaei, F. et al. "Curcumin (a constituent of turmeric): New treatment option against COVID-19", Food Sci Nutr. Sep. 6, 2020;8(10):5215-5227.
Banez, M. J. et al. "A systemic review on the antioxidant and anti-inflammatory effects of resveratrol, curcumin, and dietary nitric oxide supplementation on human cardiovascular health", Nutr Res. Jun. 2020;78:11-26.
Belcaro, G. et al. A controlled study of a lecithinized delivery system of curcumin (Meriva°) to alleviate the adverse effects of cancer treatment. Phytother Res. Mar. 2014;28(3):444-450.
Boonla, O. et al. "Curcumin improves endothelial dysfunction and vascular remodeling in 2K-1C hypertensive rats by raising nitric oxide availability and reducing oxidative stress", Nitric Oxide. Nov. 15, 2014;42:44-53.
Carter, A. "Curry compound fights cancer in the clinic", J Natl Cancer Inst. May 7, 2008;100(9):616-617.
Chen, R. et al. "Curcumin attenuates cardiomyocyte hypertrophy induced by high glucose and insulin via the PPAR?/Akt/NO signaling pathway", Diabetes Res Clin Pract. May 2015;108(2):235-242.
Choudhuri, T. et al. "Curcumin induces apoptosis in human breast cancer cells through p53-dependent Bax induction", FEBS Lett. Feb. 13, 2002;512(1-3):334-340.
Debata, P.R. et al. "A novel curcumin-based vaginal cream Vacurin selectively eliminates apposed human cervical cancer cells", Gynecol Oncol. Apr. 2013;129(1):145-153.
Dhandapani, K.M. et al. "Curcumin suppresses growth and chemoresistance of human glioblastoma cells via AP-1 and NFkappaB transcription factors", J Neurochem. Jul. 2007;102(2):522-538.
Dhar, S. et al. "Promising role of curcumin against viral diseases emphasizing COVID-19 management: A review on the mechanistic insights with reference to host-pathogen interaction and immunomodulation", J Funct Foods. Jul. 2021;82:104503, 12 pages.
Fang, W. et al., "The role of NO in COVID-19 and potential therapeutic strategies". Free Radic Biol Med. Feb. 1, 2021;163:153-162.
Farhangkhoee, H. et al. "Differential effects of curcumin on vasoactive factors in the diabetic rat heart", Nutr Metab (Lond). Jul. 18, 2006;3:27, 8 pages.

(Continued)

*Primary Examiner* — Russell G Fiebig
(74) *Attorney, Agent, or Firm* — Fox Rothschild LLP

(57) ABSTRACT

A composition and a kit comprising a nitrite source admixed with a gelling agent for nitric oxide production. Also disclosed is a method for generating nitric oxide, which finds applications in the treatment of various diseases.

19 Claims, 12 Drawing Sheets

(56) References Cited

OTHER PUBLICATIONS

Forte, M. et al. "Targeting Nitric Oxide with Natural Derived Compounds as a Therapeutic Strategy in Vascular Diseases", Oxid Med Cell Longev. 2016;Article ID:7364138, 20 pages.
Hajavi, J. et al. "Curcumin: A Naturally Occurring Modulator of Adipokines in Diabetes", J Cell Biochem. Dec. 2017;118(12):4170-4182.
Hedayati-Moghadam, M. et al. "The Role of Chemokines in Cardiovascular Diseases and the Therapeutic Effect of Curcumin on CXCL8 and CCL2 as Pathological Chemokines in Atherosclerosis", Adv Exp Med Biol. 2021;1328:155-170.
Hickey, M.A. et al. "Improvement of neuropathology and transcriptional deficits in CAG 140 knock-in mice supports a beneficial effect of dietary curcumin in Huntington's disease", Mol Neurodegener. Apr. 4, 2012;7:12, 16 pages.
Holte, P. ten, et al. "HDAC inhibition in cancer therapy: an increasingly intriguing tale of chemistry, biology and clinical benefit," Cancer. Springer, Berlin, Heidelberg, 2007. 293-331.
Jeengar, M.K. et al. "Emu oil based nano-emulgel for topical delivery of curcumin", Int J Pharm. Jun. 15, 2016;506(1-2):222-236.
Kahkhaie, K.R. et al. "Curcumin: a modulator of inflammatory signaling pathways in the immune system", Inflammopharmacology. Oct. 2019;27(5):885-900.
Kanai, M. "Therapeutic applications of curcumin for patients with pancreatic cancer", World J Gastroenterol. Jul. 28, 2014;20(28):9384-9391.
Kanai, M. et al. "A phase I/II study of gemcitabine-based chemotherapy plus curcumin for patients with gemcitabine-resistant pancreatic cancer", Cancer Chemother Pharmacol. Jul. 2011;68(1):157-164.
Kim, T. et al. "Curcumin activates AMPK and suppresses gluconeogenic gene expression in hepatoma cells", Biochem Biophys Res Commun. Oct. 16, 2009;388(2):377-382.
Lawrence, G.D. "Dietary fats and health: dietary recommendations in the context of scientific evidence", Adv Nutr. May 1, 2013;4(3):294-302.
Lim, G.P. et al. "The curry spice curcumin reduces oxidative damage and amyloid pathology in an Alzheimer transgenic mouse", J Neurosci. Nov. 1, 2001;21(21):8370-8377.
Lin, L. et al. "Targeting colon cancer stem cells using a new curcumin analogue, GO-Y030", Br J Cancer. Jul. 12, 2011;105(2):212-220.
Liu, Z. et al. "The Inhibitory Effect of Curcumin on Virus-Induced Cytokine Storm and Its Potential Use in the Associated Severe Pneumonia", Front Cell Dev Biol. Jun. 12, 2020;8:479, 10 pages.
Miao, Y. et al. "Curcumin pretreatment attenuates inflammation and mitochondrial dysfunction in experimental stroke: The possible role of Sirt1 signaling", Brain Res Bull. Mar. 2016;121:9-15.
Mukherjee, S. et al. "Liposomal TriCurin, A Synergistic Combination of Curcumin, Epicatechin Gallate and Resveratrol, Repolarizes Tumor-Associated Microglia/Macrophages, and Eliminates Glioblastoma (GBM) and GBM Stem Cells", Molecules. Jan. 18, 2018;23(1):201, 21 pages.
Mukherjee, S. et al. "Unique synergistic formulation of curcumin, epicatechin gallate and resveratrol, tricurin, suppresses HPV E6, eliminates HPV+ cancer cells, and inhibits tumor progression", Oncotarget. Mar. 29, 2017;8(37):60904-60916.
Nakmareong, S. et al. "Antioxidant and vascular protective effects of curcumin and tetrahydrocurcumin in rats with L-NAME-induced hypertension", Naunyn Schmiedebergs Arch Pharmacol. May 2011;383(5):519-529.
Nakmareong, S. et al. "Tetrahydrocurcumin alleviates hypertension, aortic stiffening and oxidative stress in rats with nitric oxide deficiency", Hypertens Res. Apr. 2012,35(4):418-425.
Oliviero, F. et al. "Anti-inflammatory effects of polyphenols in arthritis",. J Sci Food Agric. Mar. 2018;98(5):1653-1659.
Purkayastha, S. et al. "Curcumin blocks brain tumor formation", Brain Res. Apr. 17, 2009;1266:130-138.
Rattis, B.A.C. et al. "Curcumin as a Potential Treatment for COVID-19", Front Pharmacol. May 7, 2021;12:675287, 14 pages.
Rungseesantivanon et al. "Curcumin supplementation could improve diabetes-induced endothelial dysfunction associated with decreased vascular superoxide production and PKC inhibition", BMC Complementary and Alternative Medicine 2010, 10:57; 9 pages.
Satheesh A. et al., "Penetration enhancer accelerated solubilization of curcumin by poly(vinylpyrrolidone)", J. Indian Chem. Soc., vol. 96, Jan. 2019, pp. 14-18.
Sui, Z. et al. "Inhibition of the HIV-1 and HIV-2 proteases by curcumin and curcumin boron complexes", Bioorg Med Chem. Dec. 1993;1(6):415-422.
Turmeric Curcumin Topical Patches—30 Days Supply—USA Made by Live To Shine,—Amazon.com: Turmeric Curcumin Topical Patches—30 Days Supply USA Made by Live To Shine : Health & Household <https://www.amazon.com/Turmeric-Curcumin-Topical-Patches-Supply/dp/B07G94GHNV/ref=sr_1_5?crid=AICY5YTKFKLJ&keywords=curcumin+patch&qid=1647009345&sprefix=curcumin+patch%2Caps%2C69&sr=8-5>, 1 page.
Turmeric Max Patch—30 Patches—Omni Global Labs, Amazon. com: Turmeric Max Patch—30 Patches : Health & Household <https://www.amazon.com/Turmeric-Max-Topical-Patch-Patches/dp/B07K4W17NC/ref=sr_1_6?crid=AICY5YTKFKLJ&keywords=curcumin+patch&qid=1647009345&sprefix=curcumin+patch%2Caps%2C69&sr=8-6>, 3 pages.
Xu, PH. et al. "The relaxant effect of curcumin on porcine coronary arterial ring segments", Vascul Pharmacol. Jul. 2007;47(1):25-30.
Yang, F. et al. "Curcumin inhibits formation of amyloid beta oligomers and fibrils, binds plaques, and reduces amyloid in vivo", J Biol Chem. Feb. 18, 2005;280(7):5892-5901.
Zendedel, E. et al. "Impact of curcumin on sirtuins: A review", J Cell Biochem. Dec. 2018;119(12):10291-10300.
Yang et al., 'Novel nitric oxide generating platform using manuka honey as an anti-biofilm strategy in chronic rhinosinusitis', International Forum of Allergy & Rhinology, vol. 10, issue 2, Dec. 13, 2019 (13.21.2019), p. 223-232.
'Viscosity Tables', V&P Scientific, Jan. 13, 2008 (Jan. 13, 2008), 3 pages.
Margel et al. "Nitric oxide charged catheters as a potential strategy for prevention of hospital acquired infections", PLoS One. Apr. 14, 2017;12(4):e0174443. doi: 10.1371/journal.pone.0174443, 17 pages.
Karakas et al. "NO-Releasing Nanoparticles Decrease Detrusor Overactivity in DNOS−/− Knockout and Transgenic Sickle Cell Mice", PD19-06, The Journal of Urology, vol. 199, No. 4S, Supplement, May 19, 2018, e397, 1 page.
Karakus et al. "NO-Releasing Nanoparticles Ameliorate Detrusor Overactivity in Transgenic Sickle Cell Mice via Restored NO/ROCK Signaling", J Pharmacol Exp Ther. May 2020;373(2):214-219. doi: 10.1124/jpet.119.264697. Epub Mar. 6, 2020., 6 pages.
Tanner & Marks Skin Research and Technology 2008, 14: 249-260.

* cited by examiner

APPROACH TO SUSTAINED PRODUCTION AND DELIVERY OF NITRIC OXIDE AND S-NITROSOTHIOLS

CROSS REFERENCE TO RELATED APPLICATIONS

This application is a Continuation of International Application No. PCT/US21/22734 filed Mar. 17, 2021 which claims the benefit of U.S. Provisional Patent Application No. 62/991,861 filed on Mar. 19, 2020, the disclosures of all of which are hereby incorporated by reference in their entireties.

TECHNICAL FIELD

Disclosed herein is a novel approach to the production of nitric oxide and methods of treating diseases with in situ generated nitric oxide.

BACKGROUND

Nitric oxide (NO), also known as nitrosyl radical, is a free radical that is an important signalling molecule. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Some disorders or physiological conditions can be mediated by inhalation of nitric oxide. The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia.

Generally, nitric oxide can be inhaled or otherwise delivered to the individual's lungs. Providing a therapeutic dose of NO could treat a patient suffering from a disorder or physiological condition that can be mediated by inhalation of NO or supplement or minimize the need for traditional treatments in such disorders or physiological conditions. Typically, the NO gas can be supplied in a bottled gaseous form diluted in nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). Unlike NO, the part per million levels of $NO_2$ gas can be highly toxic if inhaled and can form nitric and nitrous acid in the lungs.

Thus, there exists a need for a safe and effective production of nitric oxide, which can be used for elimination of biofilm formation and treatment of various medical conditions.

SUMMARY

An aspect of this document provides a composition for generating nitric oxide. The composition includes a hygroscopic gelling agent admixed with a nitrite source, wherein the gelling agent has a viscosity ranging from about 5000 to about 15,000 centipoise, and wherein the composition has a moisture content of less than about 15%.

In some embodiments, the gelling agent is medicinal honey. In some embodiments, the composition further includes a source of S-nitrosothiol groups. In some embodiments, the composition further includes a source of thiol groups.

Another aspect of this document provides a kit for generating nitric oxide. The kit includes (a) a hygroscopic gelling agent, wherein the gelling agent has a viscosity ranging from about 5000 to about 15,000 centipoise and has a moisture content of less than about 15%; and (b) a nitrite source. In some embodiments, the gelling agent is medicinal honey. In some embodiments, the kit further includes a source of S-nitrosothiol groups. In some embodiments, the kit further includes a source of thiol groups.

A further aspect provides method of generating nitric oxide. The method includes contacting a medium comprising a nitrite source admixed with a gelling agent with or without an effective amount of water to form nitric oxide. In the absence of added water, the hydgroscopic nature of the gelling agent such as honey can pull water from the surface of the skin or a wound and thus initiate NO production. In some embodiments, the medium is administered to a subject for the treatment of a disease or condition. In some embodiments, the medium is applied to a surface area to accelerate wound healing, treat slow healing wound, treat cutaneous infections and inhibit the formation of biofilms. Other embodiments include infusing suitable mixtures into urinary catheters or directly into a bladder to prevent and/or treat urinary tract infections especially drug resistant cather associated UTI's.

MH=manuka honey (14% w/v); N=nitrite (10 mM); CLSM=confocal laser scanning microscopy. *p≤0.0001; p≤0.001; *p≤0.002

Figure 4:
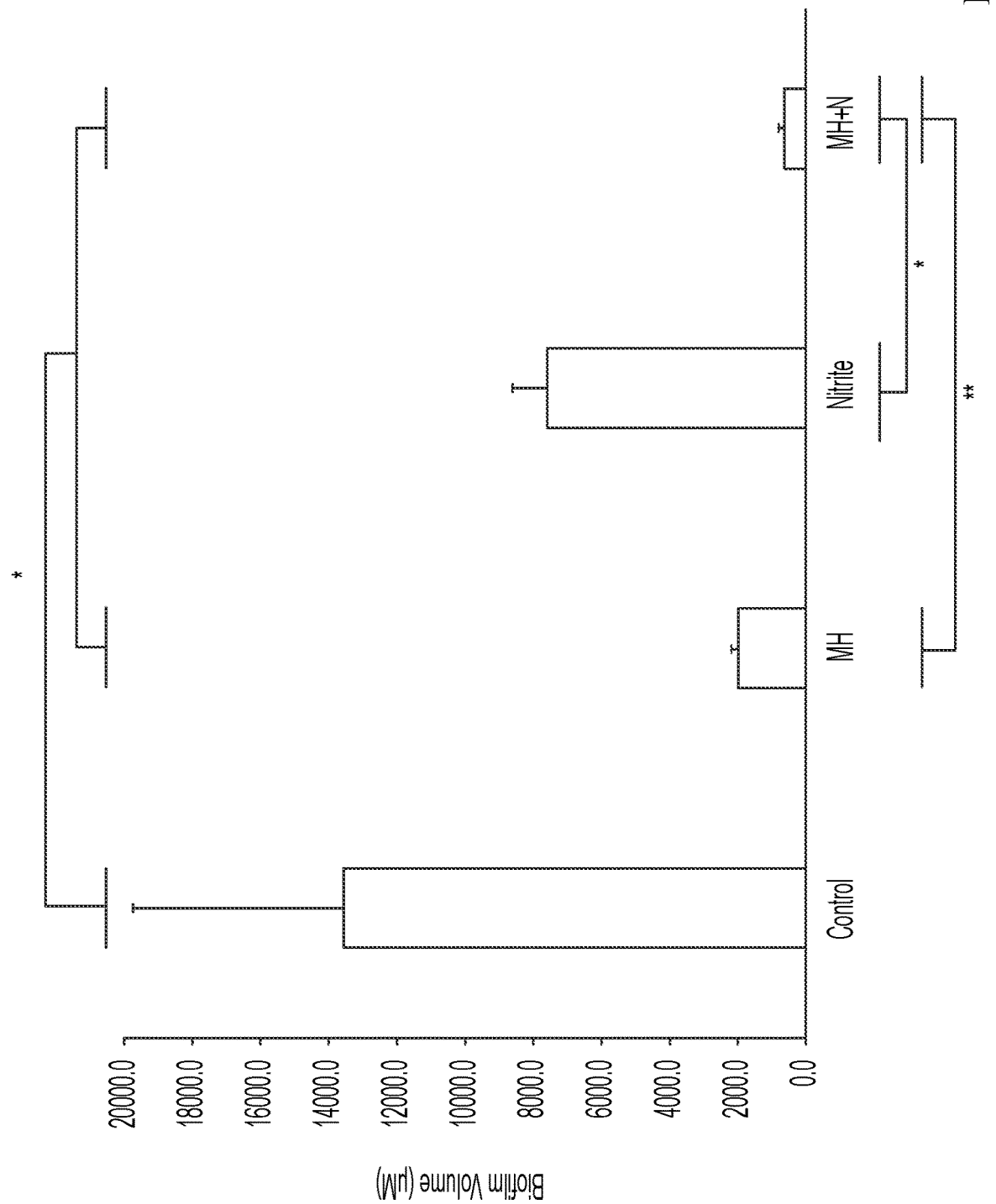

FIG. 4. Biofilm volume ($\mu m^3$) in control group and after treatment of Pseudomonas aeruginosa biofilms determined by live/dead staining and CLSM in the A) PA1 strain and C) ATCC 15692 strain. Representative CLSM images of Pseudomonas aeruginosa biofilms with 3-dimensional structures reconstructed from z-stacks in the B) PA1 strain and D) ATCC 15692 strain. Control: untreated bacteria in tryptic soy broth; MH=manuka honey (14% w/v); N=nitrite (10 mM); green=live cells; red=dead cells; CLSM: confocal laser scanning microscopy. *p≤0.0001; p≤0.001; *p≤0.002

Figure 5:
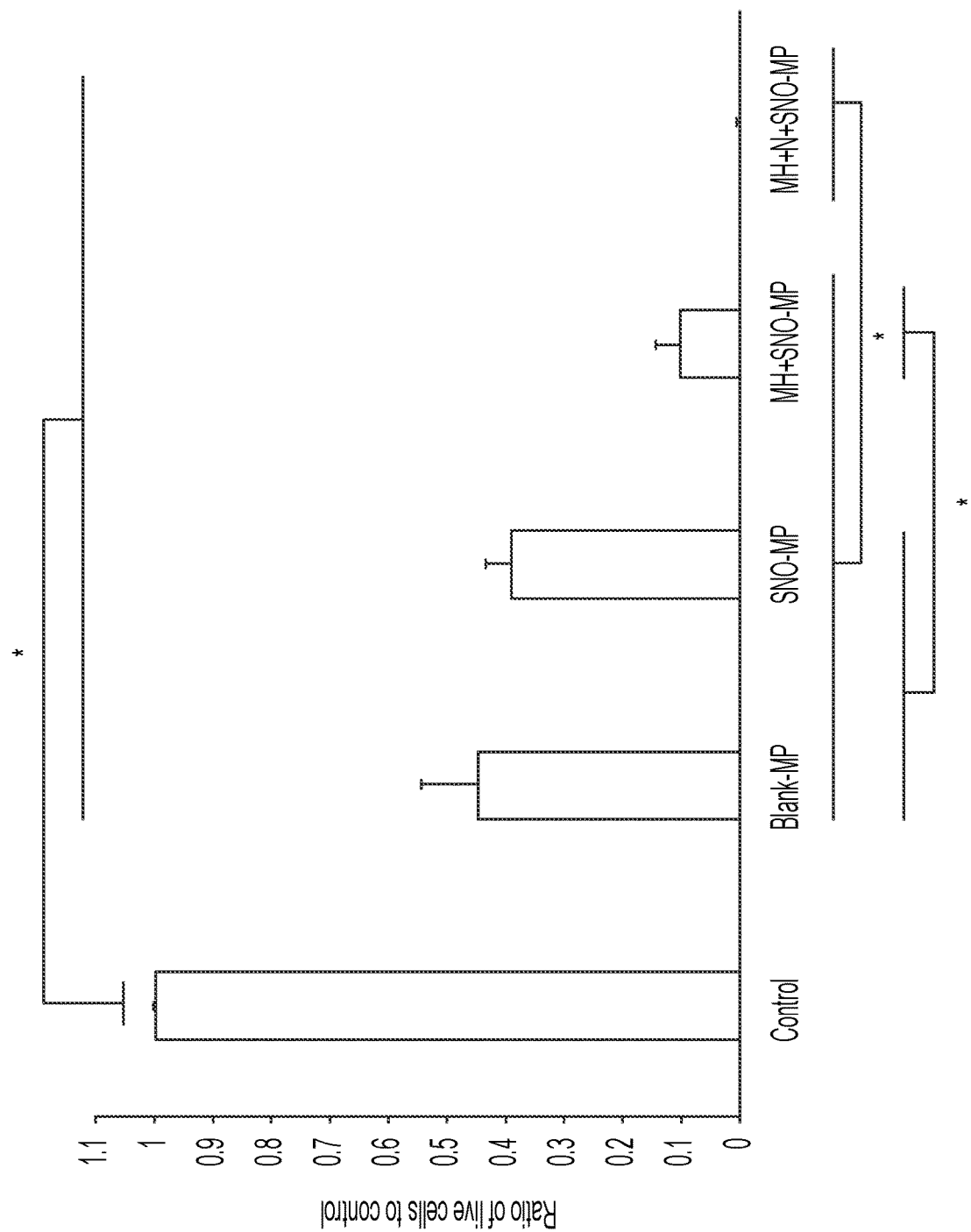

FIG. 5. Ratio of live cells in each treatment group to live cells in the control group after treatment of Pseudomonas aeruginosa biofilm determined by live/dead staining and CLSM in the A) PA1 strain and B) ATCC 15692 strain. Control=untreated bacteria in tryptic soy broth; Blank-MP: blank microparticles incapable of nitric oxide release; SNO-MP: nitric oxide-releasing microparticles; MH=manuka honey (14% w/v); N=nitrite (10 mM); CLSM=confocal laser scanning microscopy. *p≤0.0001

Figure 6:
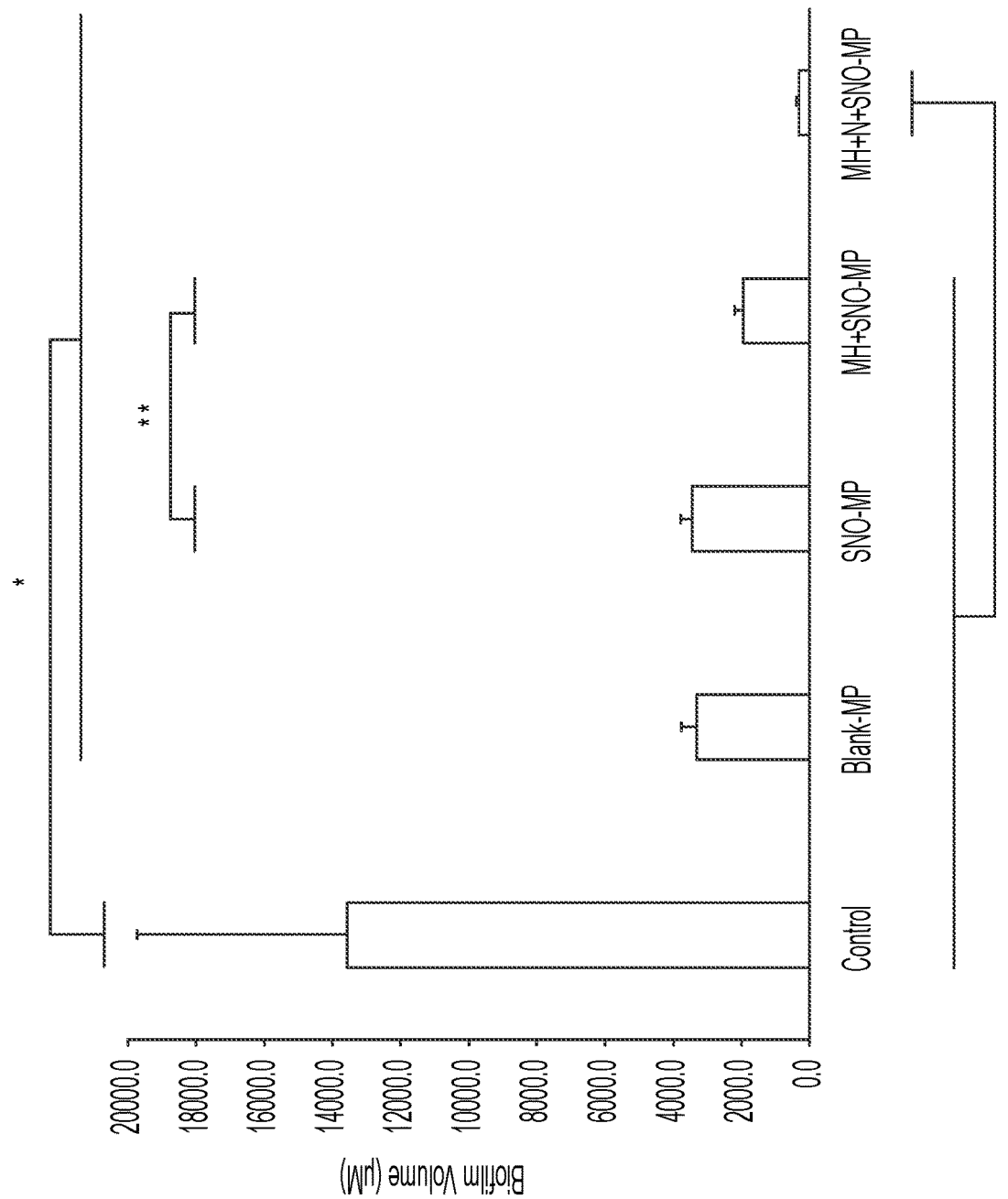

FIG. 6. Biofilm volume ($\mu m^3$) in control group and after treatment of Pseudomonas aeruginosa biofilms determined by live/dead staining and CLSM in the A) PA1 strain and C) ATCC 15692 strain. Representative CLSM images of Pseudomonas aeruginosa biofilms with 3-dimensional structures reconstructed from z-stacks in the B) PA1 strain and D) ATCC 15692 strain. Control: untreated bacteria in tryptic soy broth; Blank-MP: blank microparticles incapable of nitric oxide release; SNO-MP: nitric oxide-releasing microparticles; MH=manuka honey (14% w/v); N=nitrite (10 mM); green=live cells; red=dead cells; CLSM: confocal laser scanning microscopy. *p≤0.0001; p≤0.002; *p≤0.02

Figure 7:
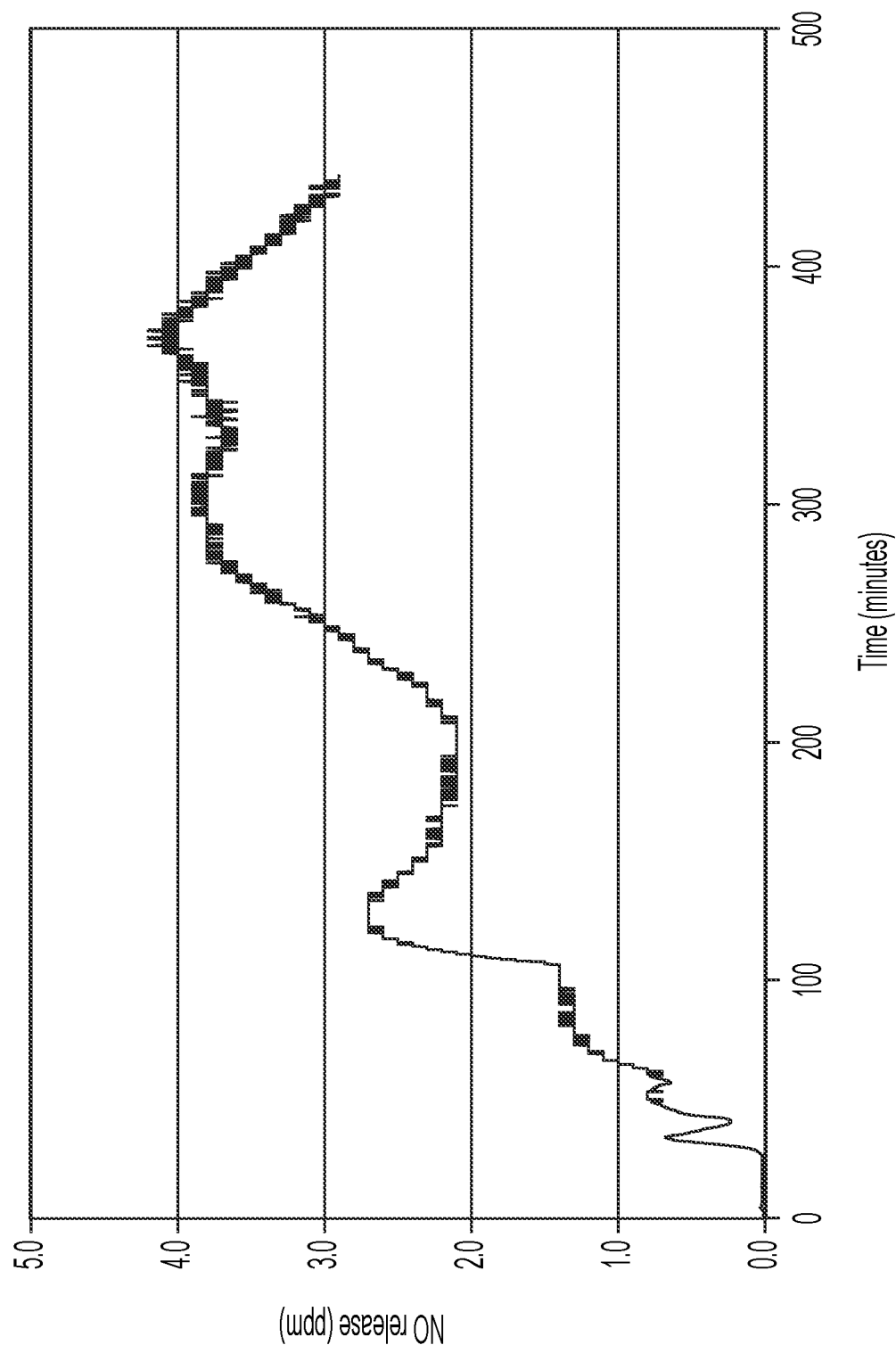

FIG. 7. Extended release of NO was achieved using alternate layers of nitrie source and NAC.

Figure 8A:
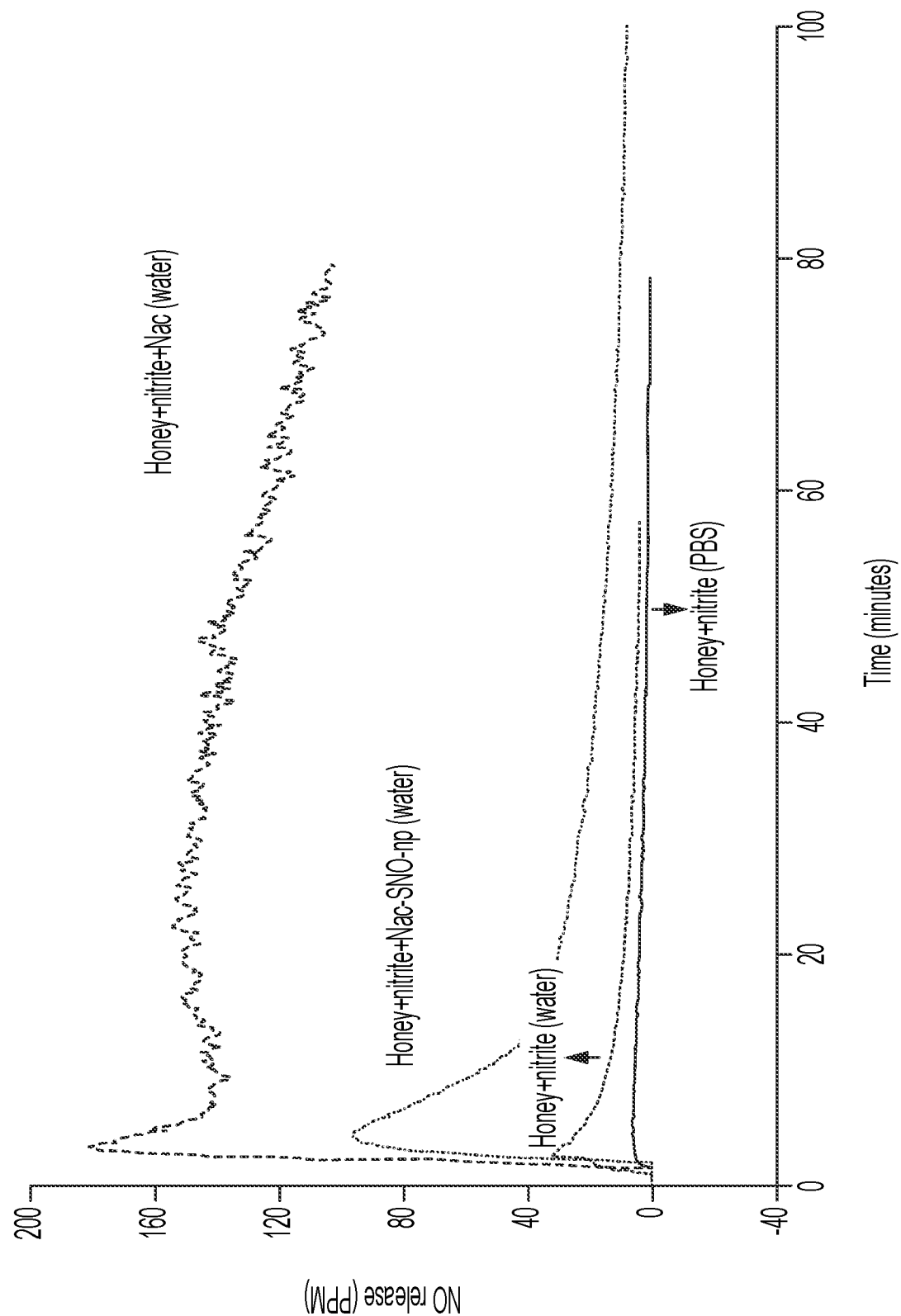
Figure 8B:
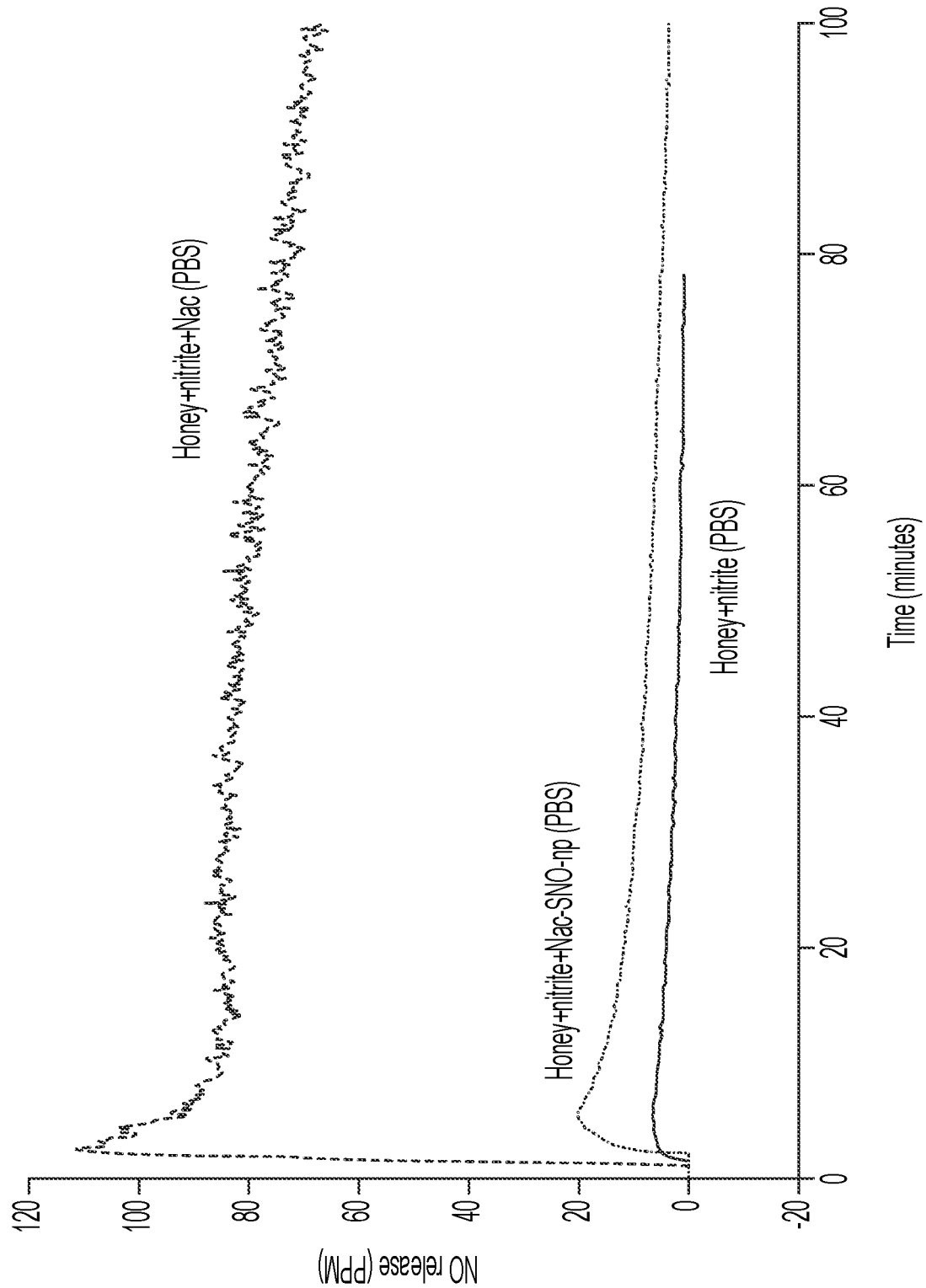
Figure 8C:
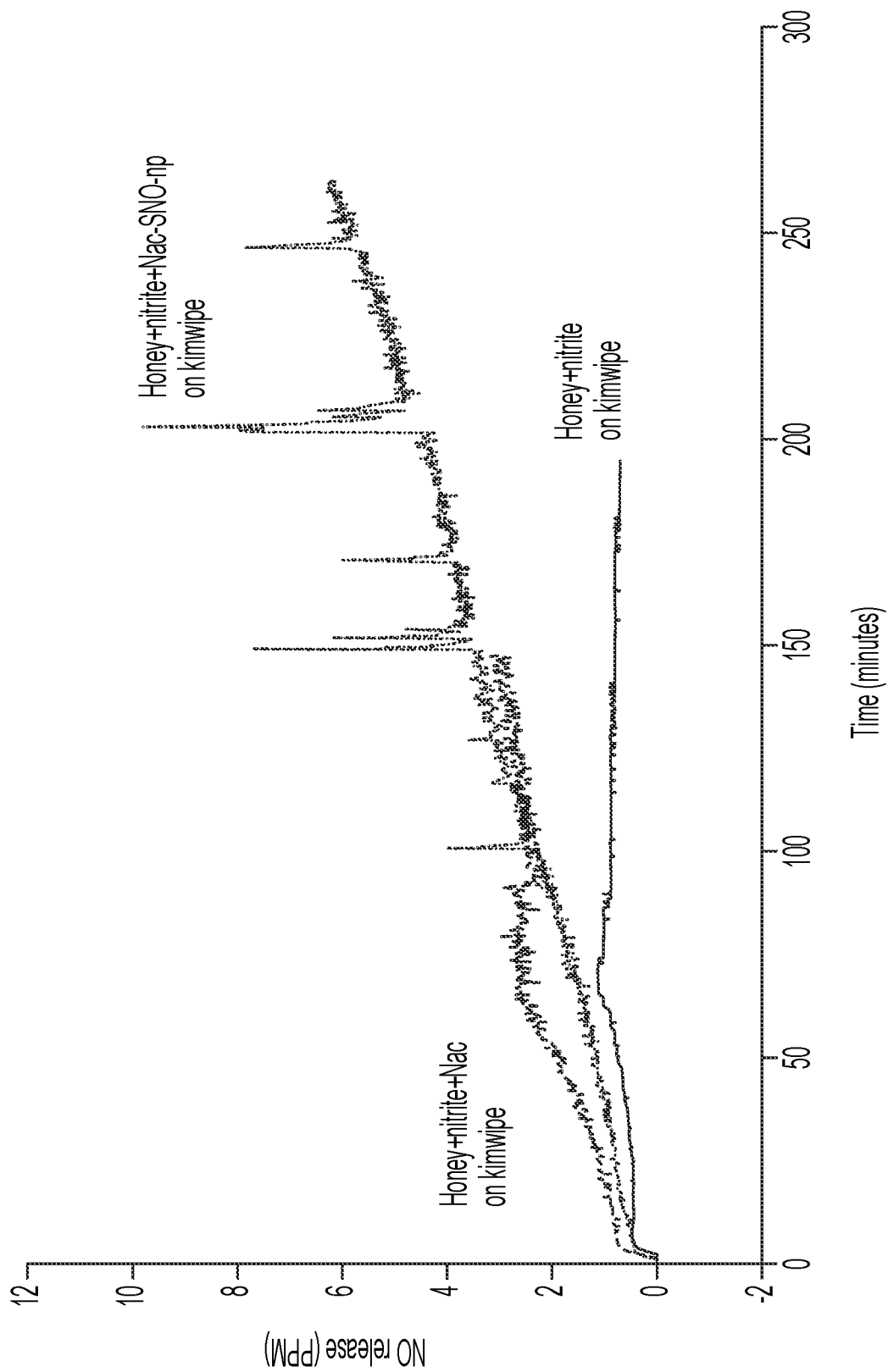

FIGS. 8A-C. Release of NO in the presence of different water sources. (a) NO release in unbuffered water. (b) NO release in PBS. (c) NO release in the present of moisture. It is anticipated from additional studies that as the nitrite concentration in the honey is increase the efficiency for producing the water initiated NO is increased due to the nature of the reaction that produces NO from protonated nitrite.

Figure 9:
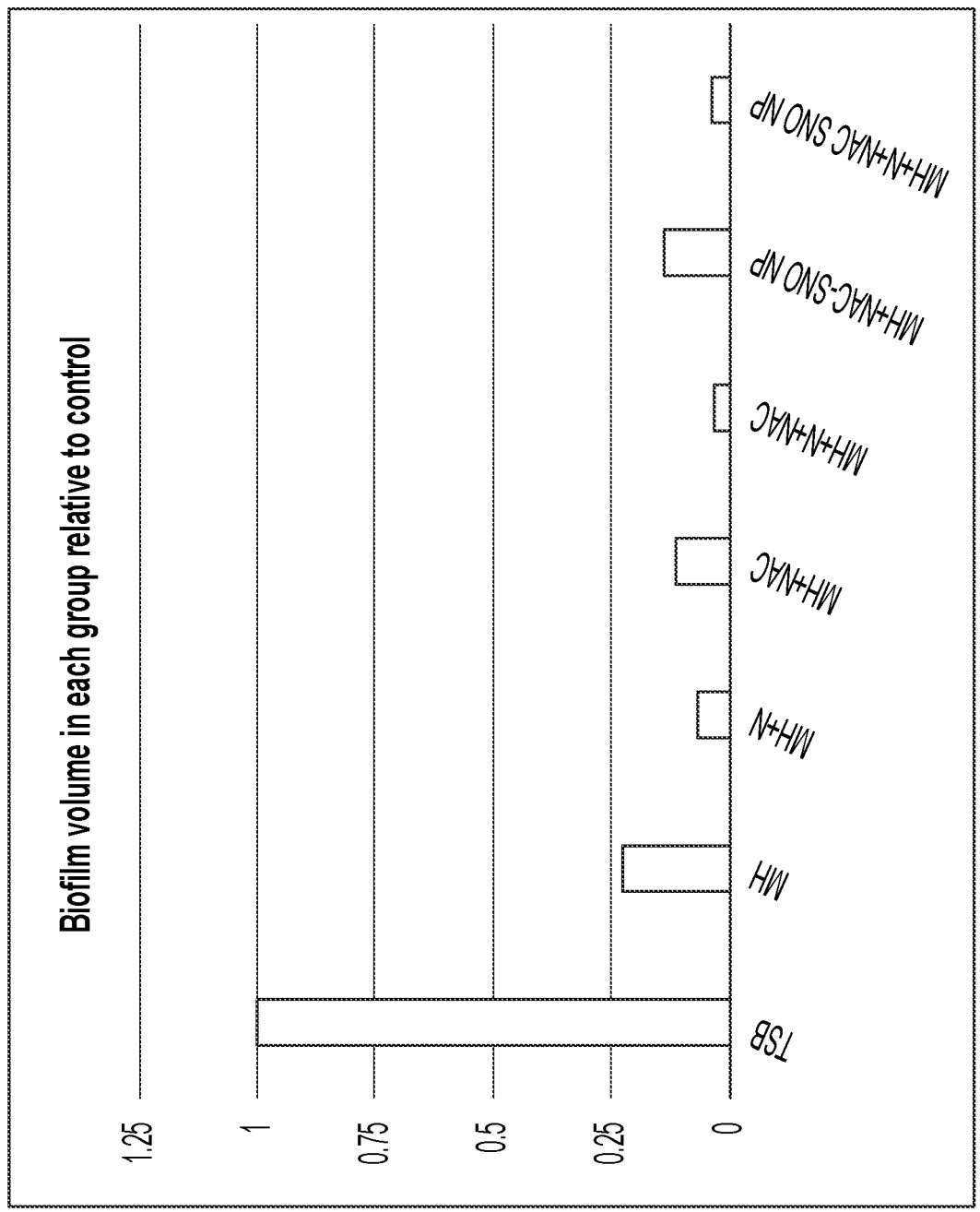

FIG. 9. Study on loss of biofilm volume (Pseudomonas a.) as a function of treatment. TSB (growth broth/control), MH (Manuka honey 14% diluted in TSB), MH+N (14% MH+sodium nitrite at 10 mM), MH(14%)+NAC (1.622 mg/ml), MH(14%)+nitrite (10 mM)+NAC (1.622 mg/ml), MH (14%)+NACSNO nanoparticles (10 mg/ml), MH+nitrite (10 mM)+NAC SNO nanoparticles (10 mg/ml).

Figure 10:
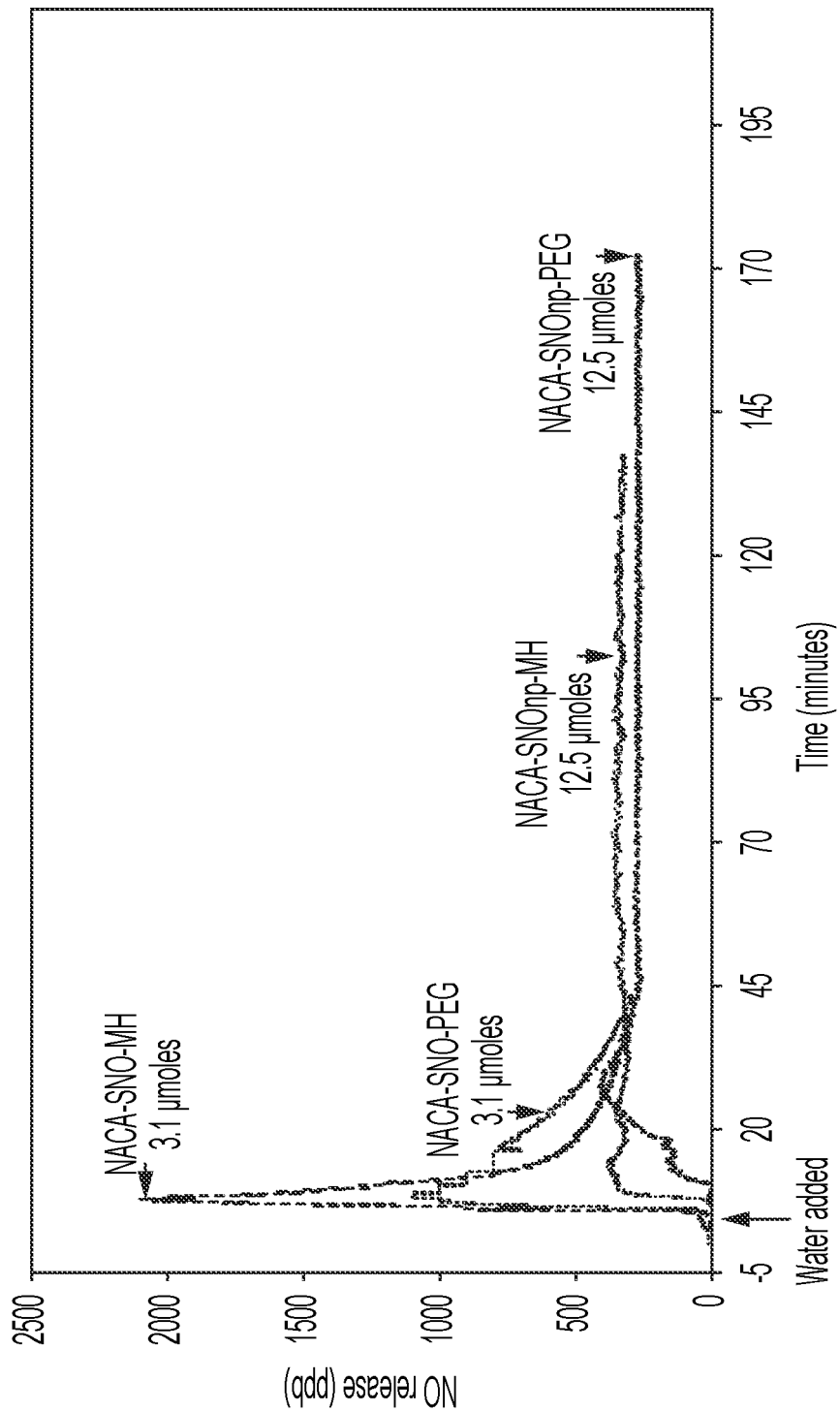

FIG. 10. The figures shows that NO release from the SNO derivative of the lipophilic amide derivative of NAC, (NAC-amide or NACA) in MH PEG400 for the free NACA-SNO and for the nanoparticle encapsulated form of NACA-SNO. The NACA-SNO nanoparticles are prepared in similar fashion to the NAC-SNO nanoparticles described in a published reference (Nachuraju et al; Nitric Oxide. 2012; 27(3):150-60. doi: 10.1016/j.niox.2012.06.003. PubMed PMID: 22705913; PMCID: 4156139.). The result shows that the combination of high viscosity solvents (MH or PEG400) with incorporation of the NO releasing molecule into a nanoparticle formulation eliminates the rapid spike phase for NO release. In aqueous solvent the release is much more rapid and less sustained.

DETAILED DESCRIPTION

Various embodiments of this patent document disclose compositions or kits for nitric oxide (NO) production. The in situ generated NO can be directly applied to the treatement of various disease or conditions. Alternatively, the NO can be stored for an extended period of time in the form of nitrosated thiols. Further, synergistic therapeutic effects have been observed when the NO generation platform incorporates additional NO releasing agents or particles.

While the following text may reference or exemplify specific embodiments of a compostion, a kit or a method relating to NO production, it is not intended to limit the scope of the compostion, kit or method to such particular reference or examples. Various modifications may be made by those skilled in the art, in view of practical and economic considerations, such as the specific source of nitrite and the amount or administration of nitrite source in combination with a gelling agent for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "C1-C18 alkyl" as used herein refers to an alkyl group containing any number (from 1 to 18 inclusive) of carbons in the alkyl group. Nonlimiting examples include methyl, ethyl, propyl, isopropyl, butyl, pentyl, and hexyl.

The term "moisture content" as used herein referes to the amount of water in a composition or formulation. A percentage describing the moisture content is by weight of the water over the total weight of the composition or formulation.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "subject" encompasses any animal, but preferably a mammal, e.g., human, non-human primate, a dog, a cat, a horse, a cow, or a rodent. More preferably, the subject is a human.

The term "pharmaceutically acceptable carrier" refers to a chemical compound that facilitates the delivery or incorporation of a compound or therapeutic agent into cells or tissues.

The term "therapeutically effective amount" or "effective amount" refers to an amount of a compound or composition effective to prevent, alleviate or ameliorate symptoms of disease, prolong the survival of the subject being treated, or reach a desirable/acceptable medical or sanitary condition. Determination of a therapeutically effective amount or effective amount is well within the capability of those skilled in the art, especially in light of the detailed disclosure provided herein.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment"

refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

I. Composition

An aspect of this document provides a compostion for generating nitric oxide. The compositon includes a hygroscopic gelling agent admixed with a nitrite source, wherein the gelling agent has a viscosity ranging from about 5000 to about 15,000 centipoise, and wherein the composition has a moisture content of less than about 15%. By sequestering the nitrite source within the gelling agent, the nitrite remains stable or dormant until being exposed to a proton source.

The low amount of moisture in the gelling agent is insufficient to initiate the production of NO formation. When the nitrite souce is in contact with water source (e.g. a buffer) or an acid source, nitrous acid is formed and then decomposes to release dinitrogen trioxde ($N_2O_3$), which can further produce NO. The production is slow or inhibited when the nitrite source is dry or when the gelling agent minimizes the contact with water. However, when water or an acid source is injected into the gelling agent in contact with the nitrite source, $N_2O_3$ and NO gas start to form. By controlling the visocosity of the gelling agent and the amount of water or the acid source, the rate and length of NO release can be controlled. Therefore, at least in some cases, the gelling agent serves to insulate the nitrite source from moisture prior to the intended NO formation and mediate at adjusted viscosity if necessary the contact with water during NO formation. In some embodiments, the moisture content in the gelling agent prior to the intended NO formation and release is less than about 15%, includes less than 10%, less than 5%, less than 2% or substantially free from water.

Various gelling agents can be used for the production of $N_2O_3$ and NO. Nonlimiting examples include honey, xanthan gum, guar gum, carrageenan gum, locust bean gum, sodium alginate, agar-agar, gelatin, modified starches, methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, co-polymers of carboxyvinyl polymers, co-polymer of acrylates, co-polymers of oxyethylene and oxypropylene and mixtures thereof. In some embodiments, the gelling agent is a reducing sugar, which can be monosaccharides (e.g. galactose, glucose and fructose), disaccharides (lactose and maltose), oligosaccharides, or polysaccharides. In some embodiments, the gelling agent is honey. Honey is generally hygroscopic and weakly acidic. A preferred type of honey is medicinal honey or Manuka honey, which is known to exhibit antibiotic activities. In particular, Manuka honey also contains methylglyoxal, which may contribute to the reduction of the nitrite to NO. The composition optionally includes other reducing agent for NO production.

The composition may also contain a dilutor for adjusting the viscosity of the gelling agent. As a result, the rate of NO production can be modified and an extended release can be achieved. In some embodiments, low molecular weight PEG (PEG 200 and PEG 400) can be combined with the gelling agent (e.g. honey) to reduce viscosity. Only upon the addition of an effective amount of water or acid source, the production of NO is initiated. Meanwhile, the dilutor (e.g. PEG) and/or the gelling agent act to provide a molecular cage surrounding NO releasing S-NO containing molecules and particles and as a result they can significantly slow the release of NO as does the enhanced viscosity of these two materials. Additional examples of dilutors include hydrophobic moleuces or polymers (e.g. petroleum jelly and K-Y jelly) or hydrophilic molecules (e.g. glycerol). In some embodiments, the PEG can serve to dissolve the nitrite to a concentration of about 100 mM, about 200 mM, about 300 mM, about 400 mM, about 500 mM, or about 600 mM. In some embodiments, the nitrite is saturated in PEG.

In some embodiments, the composition includes a combination of small and large polyalkylene glycols, which have a molecular weight (MW) difference ranging from 500 to 5000, from 1000 to 3000, from 1000 to 2000, or from 1500 to 2000 Daltons. By adjusting the ratio between the two or more polyalkylene glycols, viscosity of the composition and rate/extent of NO penetration and uptake by the circulation can be controlled. For instance, the combination may include one or both of PEG and PPG each having a MW ranging from from 100 to 2000, from from 200 to 2000, from from 400 to 1000, or from from 500 to 800 Daltons. The combination may also include one or both of PEG and PPG each having a higher MW ranging from from 800 to 5000, from from 1000 to 3000, or from from 1000 to 2000 Daltons. In further exemplary embodiments, one of polyalkylene glycols has MW of 100, 200, 400, 600, or 800, and another of the polyalkylene glycols has MW of 1000, 1500, 2000, 2500, or 3000. In some embodiments, the combination includes a PEG of 400 and a PEG of 2000 Daltons. In some embodiments, the ratio between the low MW polyalkylene glycol and the high MW polyalkylene glycol ranges from about 10:1 to about 1:10, from about 5:1 to about 1:5, from about 2:1 to about 1:2 by weight. Further exemplary ratios between the low MW polyalkylene glycol (e.g. PEG and/or PPG) and the high MW polyalkylene glycol (e.g. PEG and/or PPG) include 10:1, 8:1, 6:1, 4:1, 2:1, 1:1, 1:2, 1:4, 1:6, 1:8 and 1:10.

The ratio between the gelling agent and the dilutor can be adjusted depending on the intended use. In some embodiments, ratio by volume between the gelling agent and the dilutor ranges from about 50:1 to about 1:10, from about 10:1 to about 1:10, from about 5:1 to about 1:5, from about 2:1 to about 1:5, from about 1:1 to about 1:5, from about 1:1 to about 1:2, or from about 1:1 to about 1:3.

The nitrite source can be synthetic, natural, or a combination of synthetic and natural sources. Nonlimiting examples of the nitrite source include alkali metal nitrite, an alkaline earth metal nitrite, a transition metal nitrite and an ammonium nitrite. In some embodiments, the nitrite source is potassium nitrite, sodium nitrite, rubidium nitrite, strontium nitrite, barium nitrite, calcium nitrite, copper nitrite, zinc nitrite, or mixtures thereof. Nitrite can also be obtained from a natural source such as extracts of lettuce and spinach. The ratio between the weight of the gelling agent and the weight of nitrite depends on various factors including the specific agents and the intended applications. In some embodiments, the ratio by weight between the gelling agent and the nitrite ranges from about 50:1 to about 5000:1, from about 50:1 to about 2000:1, from about 50:1 to about 1000:1, from about 100:1 to about 1000:1, from about 200:1 to about 1000:1, from about 200:1 to about 500:1 or from about 200:1 to about 1000:1. In some embodiments, the amount of the nitrite source in the composition ranges from about 1 mg to about 5000 mg, from about 1 mg to about 1000 mg, from about 10 mg to about 500 mg, or from about 10 mg to about 100 mg.

In some embodiments, the nitrite is loaded in nanoparticles or microparticles, which are stable in the gelling agent (e.g. honey). Only when the water content increases will the nitrite be converted to NO and be released. The preparation of nitrite-loaded particles have been reported in literature, including U.S. Pat. No. 8,333,997, U.S. Patent Application No. 20160175348, and Methods Mol Biol. 2010; 704:187-95. PubMed PMID: 21161638. The entire disclosures of all these references are incorporated herein by reference. The preparation of nitrite loaded nanoparticles/microparticles under high pH conditions can prevent the acid initiated formation of NO from the nitrite. After the nitrite loaded particles are mixed with gelling agent (e.g. honey), they will remain stable/dormant until the gelling agent pulls in sufficient water to provide sufficient mobile protons to facilitate NO and $N_2O_3$ production from within the particles. Having the nitrite sequestered in the particles thus provides a more concentrated and/or more stable (with respect to generating NO prematurely) composition compared to free nitrite exposed to environment.

The composition may further contain a source of S-nitrosothiol groups. As is further illustrated in the examples, the combination with a S-nitrosothiol source can lead to synergistic antibiotic activities. Further, a sustained release of NO at higher level can be achieved. In some embodiments, the source of the S-nitrosothiol groups is nanoparticles or microparticles covalently attached to the S-nitrosothiol groups. The particles can be liphophlic, hydrophilic, or a combination of them dependending on the specific applications. In some embodiments, the size of the particles ranges from about 10 to about 2000 nm, from about 10 to about 1000 nm, from about 50 to about 1000 nm, from about 50 to about 500 nm, from about 100 to about 800 nm, from about 100 to about 600 nm, from about 100 to about 500 nm, from about 400 to about 600 nm, from about 200 to about 500 nm, or from about 20 to about 400 nm.

In some embodiments, the source of S-nitrosothiol groups is releasable molecules attached to or enclosed by nanoparticles or microparticles, and wherein the releasable molecules contain the S-nitrosothiol groups. Nonlimiting examples of the releasable molecules are selected from the group consisting of S-nitroso-Glutathione (GSNO), S-nitroso-N-acetylcysteine (SNAC), S-Nitroso-N-acetylpenicillamine (SNAP), S-nitroso-human serum albumin (SNO-HSA) or any combination thereof.

Various procedures can be employed for the preparation of SNO containing nanoparticles including for example NACSNO, GSNO, SNO-NP/MP. Exemplary procedures include those reported in Nanomedicine. 2015; 11(2):283-91. doi: 10.1016/j.nano.2014.09.017. PubMed PMID: 25461287; Journal of drugs in dermatology: JDD. 2015; 14(7):726-32. PubMed PMID: 26151790; Nitric Oxide. 2012; 27(3):150-60. doi: 10.1016/j.niox.2012.06.003. PubMed PMID: 22705913; PMCID: 4156139; and Int Forum Allergy Rhinol. 2020; 10(2):223-32. doi: 10.1002/alr.22472. PubMed PMID: 31834677. Additional reports on the preparation of SNO containing nanoparticles are available in U.S. Patent Application No. 20160175348. The entire disclosure of all of these references are hereby incorporated by reference.

In some embodiments, the source of S-nitrosothiol groups is S-nitrosothiol group-containing molecules, which include for example, S-nitroso-Glutathione (GSNO), S-nitroso-N-acetylcysteine (SNAC), S-Nitroso-N-acetylpenicillamine (SNAP), S-nitroso-human serum albumin (SNO-HAS), or any combination thereof.

The composition may further contain a source of thiol group, which can be coverted to S-nitrosothiol through a nitrite based reaction such as a reaction with dinitrogen trioxide derived from the nitrite reaction with water. The source of thiol group may be nanoparticles or microparticles having the thiol groups covalently bonded to the backbone structure of the particle thereto or releasable molecules (e.g. Glutathione, N-acetylcysteine, N-acetylpenicillamine, human serum albumin containing the thiol groups).

The thiol source such as glutathione or N-acetylcysteine can be modified to the corresponding ester or amide (e.g. C1-C18 alkyl esters of NAC as well as amides of NAC), which is more lipophilic than NAC and hence useful for cell penetration application. The source of thiol group may also be molecules containing the thiol group (e.g. Glutathione, N-acetylcysteine, N-acetylpenicillamine) without nanoparticles or microparticles, and also include for example thiol containing hydrogel based nanoparticles or microparticles and thiol coated paramagnetic and ferromagnetic nanoparticles or microparticles. For instance, thiol containing molecules can be included in honey or honey-PEG mixtures to provide a source of thiols for the production of S-nitrosothiols derived from the water initiated nitrite reaction in the nitrite loaded particles.

The mole ratio between the nitrite and SNO-containg molecule/particle or between the nitrite and thiol-containing particle or molecule ranges for example from about 10:1 to about 1:10, from about 5:1 to about 1:5, from about 2:1 to about 1:5, from about 1:1 to about 1:5, from about 1:1 to about 1:2, or from about 1:1 to about 1:3. By controlling the mole ratio, the relative amplitudes for a burst phase of NO release can be controlled and and a sustained release phase can be achieved with desirable rate of NO generation.

The composition may also contain one or more physiologically acceptable carriers, diluents, excipients, including for example, smoothing agents, suspension agents, film forming substances, and coating assistants, or a combination thereof; and a composition disclosed herein. For instance, the composition may include other excipients such as aqueous buffers, petroleum jelly and K-Y jelly for specific indications.

Acceptable additional carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, fragrances, flavoring agents, and the like may be provided in the composition.

The composition may be in the form of a suspension, a solution, a foam, a spray, an ointment, a cream, and an aerosol for administration to a subject in need. The composition may also be prepared or packaged into a discrete solid dose unit including, but not limited to, a tablet, a hard or soft capsule, a cachet, a troche, an ampule, or a lozenge, each containing a predetermined amount of the nitrite source, the gelling agent, and other suitable components, wherein the coating of these dose unit starts to disintegrate upon contact with water or physiological environment in a subject and allows the NO production to take place. Additional pharmaceutically acceptable carrier can be added to the composition to facilitate the manufacturing or storage of the compostion and the delivery of NO to the subject in need. For instance, when the composition is formulated for topical application, an oil medium such as peanut oil, liquid paraffin, or olive oil can be incorporated into the composition. A formulation for topical application may also be in a form such as a patch, a swab, a nebulizer, a sprayer, a sponge or a breakable pouch. In some embodiments, a composition is disposed in a suitable form or supportive medium, which may have one or more layers for purpose of insulating, sequestering, backing or enclosing the composition. For instance, the form or medium (e.g. a patch) can load the composition and/or limit or even prevent access of the particles to skin but allow for the production of diffusible active agents including NO and S-NO containing molecules that would access the skin.

The composition may contain various additional ingredients including, but not limited to, antioxidants, antibiotics, antifungal agents, and/or preservatives.

The compostion may be prepared, packaged, or sold in a formulation suitable for pulmonary administration via the buccal cavity. For instance, the compostion can be administered nasally as a spray derived by mixing the nitrite-loaded honey with or without nanoparticles or microparticles into a PEG and/or water containing solvent suitable for a nebulizer or atomization device. The droplets provided by this route of administration preferably have an average diameter in the range from about 0.1 to about 200 nanometers.

The compositions described herein may be prepared, packaged, or sold in formulations suitable for oral, rectal, vaginal, parenteral, topical, pulmonary, intranasal, buccal, ophthalmic, or another route of administration. In general, at least a portion of the nitrite source is not in contact with water or physiological environment in the subject prior to the administration of the formulated composition to the subject. Preferably, the nitrite source is substantially admixed with the gelling agent. Even more preferably, the nitrite source is substantially distributed or entrapped within the gelling agent. An extended or sustained release of NO is mediated through the gelling agent which controls the exposure of the nitrite source to water or physiological environment and the release of in situ formed gas.

In some embodiments, the composition is configured to provide an extended release of NO over a period of at least 30 minutes, at least 1 hour, at least 2 hours, at least 4 hours, at least 8 hours, at least 12 hours, at least 16 hours, or at least 24 hours.

II. Kit

Another aspect of the patent document provides a kit for generating NO. Besides instructional material, the kit generally includes (a) a hygroscopic gelling agent, wherein the gelling agent has a viscosity ranging from about 5000 to about 15,000 centipoise and has a moisture content of less than about 15%; and (b) a nitrite source. The gelling agent and the nitrite source can be admixed with each other or physically separated from each other in the kit. Both components should have little or low amount of water content prior to initiation of NO formation. The scope and relative amount of the gelling agent and the nitrite source are as described above. In some embodiments, the gelling agent is medicinal honey.

The instructional material of the kit may, for example, be affixed to a device or medium which contains the components of the kit. Alternatively, the instructional material may be shipped separately from the device or medium with the intention that the instructional material and other components of the kit be used cooperatively by the recipient. Various ratios between the components of the kit are as described above.

The kit may also contain a dilutor for adjusting the viscosity of the gelling agent. The dilutor can be mixed with one or both of the above components prior to NO formation. Alternatively, the dilutor can be physically separate from both of the above components and is only added to the mix just prior to the reaction.

In some embodiments, the kit also includes a source of S-nitrosothiol groups. The source can be nanoparticles or microparticles covalently attached to the S-nitrosothiol groups. The source can also be releasable molecules, which contain the S-nitrosothiol groups and are attached to or enclosed by nanoparticles or microparticles. Further, the source can be S-nitrosothiol group-containing molecules without nanoparticles or microparticles. The scope of the nanoparticles or microparticles and S-nitrosothiol group-containing molecules are as described above. Without being bound to any particular theory, it is hypothesized that the formation of $N_2O_3$ and NO from nitrite can re-nitrosate the thiyl radicals in the molecules or nanoparticle, refreshing the nitrosothiol groups, and allowing for a boost in NO release from S-nitrosothiol-containing molecules or SNO-nanoparticles or microparticles.

In some embodiments, the kit also includes a source of thiol group, which can be coverted to S-nitrosothiol. The source of thiol group may be nanoparticles or microparticles having the thiol groups covalently thereto or releasable molecules (e.g. Glutathione, N-acetylcysteine, N-acetylpenicillamine, human serum albumin containing the thiol groups). The source of thiol group may also be molecules containing the thiol group without nanoparticles or microparticles. The scope of the nanoparticles or microparticles and thiol-containing molecules are as described above. The mole ratio between the nitrite and SNO-containg molecule/particle or between the nitrite and thiol-containing particle or molecule is similar as described above.

In some embodiments, the kit further includes one or more components including water, an acid source and/or a reducing agent, which may facilite the NO production process. The component containing water or the acid source is preferably separate from the other components prior to NO production. The acid source is preferably a weak acid or a diluted acid. By controlling the amount of water or the acid source, the rate of NO production can be controlled. This is also useful when the generated gas is to be stored (e.g. conversion of NO to S-nitrosothiol group in the presence of thiol group for extended storage). In some embodiments, the ratio by weight between the gelling agent (e.g. MH) and water source ranges from about 1:10 to about 100:1, from about 1:10 to about 1:00, from about 1:50 to about 1:100, from about 1:10 to about 1:5, from about 1:10 to about 1:5, or from about 1:5 to about 1:2.

The pH of the water source may impact the rate of NO release. In some embodiments, the pH of the water source ranges from about 6 to about 8, from about 6.5 to about 7.5, or from about 6.5 to about 7. In some embodiments, the pH of the water source is 6, 6.2, 6.3, 6.4, 6.5, 6.6, 6.7, 6.8, 6.9, 7, 7.1, 7.2, 7.3, 7.4, or 7.5.

The kit may contain various additional ingredients including, but not limited to, antioxidants, antibiotics, antifungal agents, and/or preservatives.

Nonlimiting exemplary combinations of different components in the kit are provided below. Components in the same bracket are admixed with each other. Components not in the same bracket are physically separate from each other prior to the NO production or do not have substantive interaction for NO formation. (Abbreviations: H-honey, N-nitrite, RSH-thiol containing molecule (e.g. GSH, NAC), SHnp/mp-nano or microparticle with covalently attached thiol groups, RSHnp/mp-nano or microparticles with releasable thiol containing molecules (e.g. GSH, NAC), SNOnp/mp-nano or microparticle with covalently attached S-nitrosothiol groups, RSNOnp/mp-nano or microparticle with releasable molecules having S-nitrosothiol groups (e.g. GSNO, SNAC, SNAP), PEG (e.g. PEG400 and/or PEG200)
1. H+N with or without PEG
2. H+{PEG+N}
3. H+R−SH+N±PEG
4. H+{PEG+N+RSH}
5. {H+RSH}+{PEG+N}
6. {H+N}+{PEG+RSH}
7. H+{PEG+N+RSHnp/mp}
8. {H+RSHnp/mp}+{PEG+N}
9. {H+N}+{PEG+RSHnp/mp}
10. H+{PEG+N+SHnp/mp}
11. {H+SHnp/mp}+{PEG+N}
12. {H+N}+{PEG+SHnp/mp}
13. H+{PEG+N+RSNOnp/mp}
14. {H+RSNOnp/mp}+{PEG+N}
15. {H+N}+{PEG+RSNOnp/mp}
16. H+{PEG+N+SNOnp/mp}
17. {H+SNOnp/mp}+{PEG+N}
18. {H+N}+{PEG+SNOnp/mp}

In compositions or kits disclosed in this patent document, the nitrite concentration after mixing with the gelling agent (e.g. Manuka honey) and optionally with other agent (e.g. diluting agent such as PEG) can be adjusted depending on the intended use. In some embodiments, the concentration of the nitrite is more than 1 M, more than 2 M, more than 3 M, more than 4 M, more than 5 M, more than 6 M, or more than 7 M.

In an exemplary embodiment, a compostion or a kit (e.g. single or multiple layered bandage) containing (1) Manuka honey admixed with nitrite and (2) a thiol source (e.g. GSH or NAC) can be applied to skin and to the toe nail for treating wound lesions or toe fungus. SNO is formed from both GSH and NAC in response to NO generation as moisture is pulled into the composition or kit (e.g. bandage).

Accordingly, different components of the kit may be in contact with each other or physically separate from each other. Depending on the specific configuration and the intended application, the kit may have 1, 2, 3 or more groups of components, where each group is not in direct contact with each other or the contact is insufficient to initiate the formation of NO. For instance, a sealed bandage may contain a mixture of honey, nitrite source and PEG and does not activate NO generation until being exposed to water or physiological environment in a subject. Alternatively, the nitrite may be mixed with PEG in one layer of the bandage and honey is impregnated in another layer, wherein the two layers have minimum interaction until pressed together and being exposed to a water or acid source, which can be present in a physiological environment (e.g. skin, scalp, mucosa, or gums) or available from an additional component of the kit.

Other non-limiting examples of the kit include single or multiple layered dressing, single or multiple layered film, sprayer or nebulizer, tube, cartridge, syringe, each of which contain the nitrite source, the gelling agent, and one or more of the above described components.

III. Method of Generating Nitric Oxide

The method of NO production generally includes contacting a medium comprising a nitrite source and a gelling agent with an effective amount of water to for a sufficient period of time to generate nitric oxide. The nitrite source and the gelling agent are as described above and are mixed together or seprate from each other prior to NO production. The ratio by weight between the gelling agent (e.g. MH) and water source is as described above.

The medium can be the composition described in this patent document. Nonlimiting examples of the specific forms of the composition as a medium include suspension, solution, gel, cream, and ointment, each of which contains the nitrite source and the gelling agent.

The medium can also be a substrate or part of the kit described above. For instance, a wound dressing, a bandage or a film impreganated with the nitrite source and the gelling agent can serve as the medium. The medium may include different sections or additional components as described for the kit above. These sections or components are brought together to provide a single medium. In exemplary embodiments, two separate strips, bandages, or films containg separate components of the example combinations 1-18 of the kit described above are pressed together to form a band as a common medium, and upon exposure to a water source or physiological environment in a subject NO production is initiated from the medium.

The method is effective for generating a material capable of sustained NO release over a wide range of time scales. The method can be applied to generating, stabilizing and storing S-nitrosothiol containing materials (e.g. nanoparticles or microparticles). In some embodiments, the medium also contains a source of S-nitrosothiol groups. In some embodiments, the medium also contains a source of thiol groups. The scope of the source of S-nitrosothiol groups and source of thiol groups are as described above.

The method allows for a sustained generation of NO and thus provides maximum effects for various medical or sanitary needs. In some embodiments, an effective amount of NO is released over a period of more than 5 minutes, more than 10 minutes, more than 20 minutes, more than 40 minutes, more than 60 minutes, more than 90 minutes, more than 2 hours, more than 3 hours, more than 4 hours, more than 6 hours, more than 12 hours, more than 18 hours, or more than 24 hours.

The amount of water source can be controlled to adjust the rate of NO release. In some embodiments, the amount of water or acid ranges from about 0.2 to about 10 equivalents of the nitrite source, from about 0.5 to about 10 equivalent of the nitrite source, from about 0.2 to about 5 equivalent of the nitrite source, from about 0.5 to about 10 equivalent of the nitrite source from about 1 to about 5 equivalent of the nitrite source, from about 0.5 to about 2 equivalent of the nitrite source, or from about 0.5 to about 1.5 equivalent of the nitrite source.

The temperature of the medium is relevant to the viscosity of the gelling agent and the release of NO. Lower temperature also allows for extended storage of NO, for example after formation of an S-nitrosothiol group from thiol group. In some embodiments, the temperature ranges from about 20° C. to about 50° C., from about 20° C. to about 40° C., from about 20° C. to about 30° C., from about 0° C. to about 30° C., from about 0° C. to about 20° C., from about 0° C. to about 10° C., or from about −10° C. to about 0° C.

In some embodiments, the method provides an extended release of NO over a period of at least 10 minutes, at least 30 minutes, at least 1 hour, at least 2 hours, at least 4 hours, at least 8 hours, at least 10 hours, at least 15 hours, at least 20 hours, at least 1 day, at least 2 days, at least 3 days, at least 5 days, or at least 1 week.

As shown in the examples, the compositions and kits disclosed herein also allow for storage/stabilization of SNO containing molecules or nano/micro particles for extended periods of time. For instance, minimum NO release is observed for samples of SNO mp and NACSNO np stored in Manuka honey plus PEG400 prior to an intended NO release for the desired purpose. In some embodiments, prior to an intended NO release less than 5%, less than 10%, less than 15%, less than 20%, or less than 25% of SNO containing molecules or nano/micro particles releases NO over a period of more than 1 month, more than 3 months, more than 6 months, more than 9 months, more than 12 months, or more than 24 months from the composition or kit disclosed in this patent document. When needed, the compositon or kit can be activated to generate NO (immediate release or extended release) at a desirable rate.

Inhibition of Biofilm Growth

In some embodiments, the method is directed to inhibition of biofilm growth. Biofilms are a major factor in creating drug resistance due to limiting drug access to the organisms and creating an interactive environment that facilitates the transmission of drug resistance through the community within the biofilm. Biofilms are also etiologic agents for a number of disease states in mammals. Otitis media, dental plaque, bacterial endocarditis, cystic fibrosis and Legionnair's disease along with a broad array of hospital acquired, dental and medical clinic infections are examples of its pathology. Bacteria growing in biofilms display increased resistance to antibiotics. Commonly surveyed microbial organisms that form biofilms are *Burkholderia cenocepacia, Staphlococcus, Steptococccus, Pseudomonas*, and *Legionnella* and their subtypes.

In some embodiments, the medium includes S-nitorsothiol group-containing nanoparitcles or microparticles. As illustrated in the examples, synergistic results can be achieved when NO is generated from a nitrite source in combination with the use of NO-relasing particles. The medium can be applied to any surface or substrate for bacterial eradication and disinfection purposes. For instance, a medium containing the gelling agent, the nitrite source and NO-releasing particles in a suitable form (e.g. suspension, mist, gel, cream, bandages, or dressings) can be sprayed, pasted, attached to the surface of skin or medical instrument or any target area to prevent or inhibit bacterial growth. Additional nonlimiting examples of surfaces or areas to be treated include air and/or water heating/cooling distribution systems in facilities such as hospitals and laboratories, surfaces of medical devices, household surfaces, dental plaque, dental and/or medical water treatment lines, industrial pipelines, water treatment and distribution facilities and fluids sterilization. Various suitable delivery apparatus can be designed to facilitate nitric oxide gas administration to each specific unique application.

Treatment of Diseases

In some embodiments, the method is directed to the treatment of a disease in a subject, comprising administering to the subject a medium described herein which contains a nitrite source admixed with a gelling agent, wherein a therapeutic effective amount of nitric oxide is generated after the medium is exposed to a water source.

In some embodiments, the medium contains a source of S-nitrosothiol groups. As is further illustrated in the examples, the combination with a S-nitrosothiol source can lead to synergistic antibiotic activities. Further, a sustained release of NO at higher level can be achieved. In some embodiments, the source of the S-nitrosothiol groups is nanoparticles or microparticles covalently attached to the S-nitrosothiol groups. In some embodimetns, the source of S-nitrosothiol groups is releasable molecules attached to or enclosed by nanoparticles or microparticles, and wherein the releasable molecules contain the S-nitrosothiol groups. Nonlimiting examples of the releasable molecules are selected from the group consisting of 5-nitroso-Glutathione (GSNO), S-nitroso-N-acetylcysteine (SNAC), S-Nitroso-N-acetyl-penicillamine (SNAP), S-nitroso-human serum albumin (SNO-HAS) or any combination thereof.

The method is applicable to the treatments various diseases or conditions. Nonlimiting examples include pulmonary hypertension, skin/dermatological conditions (acne, inflammatory skin conditions, raynaud's disease, pain, post herpetic lesions, shingles, infections (e.g. skin infections, catheter (IV catheters, urinary caheters, etc) induced infections), inflammatory conditions, chronic rhinosinusitis, wounds, burns, leg ulcers (sickle cell, diabetic), onychomycosis), peripheral vascular disease, infected and/or inflamed mucosal tissues (periodontal disease, rectal/anal lesions, vaginal lesions), erectile dysfunction, female sexual dysfunction and vaginal infections/inflammation, catheter associated urinary tract infection, sinusitis, cystic fibrosis, acute respiratory distress syndrome, pulmonary fibrosis, chronic obstructive pulmonary disease (COPD), bronchiectasis, pulmonary infections including tb, pulmonary hypertension, and burns and other open wounds, inner and/or outer ear infections, gastric and intestinal diseases (ulcers, infections and inflammatory conditions), acute vascular inflammatory conditions (Hemorrhagic shock, Hemorrhagic fevers, Acute sickle cell crisis). In more examples, the method provides NO as an additive to organ perfusion fluids for stored organs, or to transfusion materials to minimize inflammation, enhance tissue perfusion and stabilize red blood cells.

The method provides effective wound care in a subject with or without infections. For instance, NO generated in the medium described herein accelerates wound closure and promotes the formation of normal strong collagen in contrast to the weaker collagen associated with scar tissue. When the therapeutic medium is topically delivered, it effectively counters excessive inflammation. NO when not produced by inflammatory cells such as macrophages is anti-inflammatory. Without being bound by any particular theory, it is postulated that NO generated from the medium will repolarize activated macrophages from the cytotoxic population to the repair/non-toxic population.

In wound care for subjects having infections, NO delivered via the method of this patent document exhibits very broad antimicrobial activity. It efficiently kills gram negative and gram positive bacteria, and fungi (including Candida auris-unpublished results from our lab). Most significant is that NO is effective against ESKAPE organism that are the source of much concern due to their resistance to conventional antimicrobial therapies. There are indications that it has antiviral activity as well.

The method is also effective against slow healing or hard to treat wounds such as leg ulcers (e.g. ulcers due to diabetic condition or sickle cell), burns infected with biofilm producing organisms (e.g. Candida), and cellulitis. Additional infections or conditions treatable with the method includes drug resistant Urinary tract infections, ear infections (e.g. Otitis media and externa, and infections associated with tube insertion into the ear drum and other myringotomies), Onychomycosis, acne, Styes and chalazia, Chronic drug resistant sinusitis, and Cystic fibrosis.

Treatment of inflammatory conditions is another application of the medium described in this patent document. Nonlimiting examples include pulmonary inflammatory conditions (inhalable formulations, e.g. acute repertory distress syndrome and asthma) and vascular inflammatory conditions (iv infusion formulations, e.g. septic shock, hemorrhagic shock, hemorrhagic fevers, ischemia reperfusion injury, acute sickle cell crisis, transfusion associated vascular inflammation and toxicity).

In some embodiments, the method is applied to the treatment of pulmonary consequences or symptoms of viral infections. For instance, the medium or composition described herein provides an effective amount of NO for treating coronavirus (COVID-19) associated symptoms such as coughing and difficulty with breathing.

Other applications of NO generation described herein include blood storage, organ perfusion, and treatment of ophthalmological conditions. Treatment of blood with NO during storage or prior to transfusion to enhance therapeutic efficacy and safety. Infused NO releasing honey minimizes cellular damage to stored organs (liver, kidney, lung) due to oxidative stress and anti-inflammatory activity and enhances tissue perfusion. NO is also known to reduce ocular pressure and thus can be used to treat glaucoma. Further, because NO is anticipated to have a positive impact on dry eye through multiple pathways including antiinflammatory activity and direct effect on the tear duct, the NO generation method of this patent document can be used to treat dry eye.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

For topical (e.g. skin, mucosal, gum, scalp, or nail) administration, penetrants appropriate to the barrier to be permeated may be used. For instance, penetration enhancers such as myristic acid can be incorporated to the medium to facilitate skin penetration of released nanoparticles or microparticles. Nonlimiting examples if delivery devices or kits include NO releasing bandages and wound packing materials, NO releasing bandages/band aids, NO releasing spread on creams and gels, and NO releasing spray.

Injectables can be prepared in conventional forms, either as liquid solutions or suspensions, solid forms suitable for solution or suspension in liquid prior to injection, or as emulsions. The composition disclosed herein can also be infused into medical devices such as bladder and urinary catheter.

For administration by inhalation, the medium containing the nitrite source and the gelling agent can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. For instance, a nebulizer or nasal spray can be used for the delivery of NO generating medium or compostion for treating respiratory conditions, including coronavirus or sinusitis.

For rectal administration, the medium may also be in the form of suppositories or retention enemas, e.g., containing conventional suppository bases such as cocoa butter or other glycerides.

Various devices or kits can be adopted for the delivery of NO depending on the specific diseases/conditions and suitable routes of administration. For instance in dual plunger based systems, different compositions of reduced viscosity honey (diluted with PEG or other suitable non-aqueous liquids) thiols and/or thiol/nitrosothiols containing nanoparticles are mixed with nitrite containing solutions in PEG, PEG with varying amounts of water or just water. For bandages or band aids with two overlapping breakable compartments, they can be broken with finger pressure to allow for the mixing of the contents of two chambers. The addition of water due to the hygroscopic nature of the honey pulling in fluid from the skin and or wound would initiate the robust formation of NO and SNO containing materials (e.g. GSNO, NACSNO, SNO containing nano/micro particles). Thiols and thiol containing particles are stable in the honey. NO release from SNO containing molecules and SNO containing particles is extremely slow in the presence of only PEG. A water source is needed to initiate release. In an exemplary embodiment of a device/kit containing Chamber 1 and Chamber 2, Chamber 1 contains one or more of (a) one of more thiols (e.g. NAC, NAC alkyl esters (to increase the lipophilicity of the NAC for enhanced access across cell membranes), GSH, albumin, and penicillamine), (b) thiol containing nano and microparticles, and (c) nitrosothiols containing nano or microparticles; Chamber 2 contains PEG admixed with a nitrite source.

As will be readily apparent to one skilled in the art, the useful in vivo dosage to be administered and the particular mode of administration will vary depending upon the age, weight and mammalian species treated, the particular agents or components employed, and the specific target use. The determination of effective dosage levels, that is the dosage levels necessary to achieve the desired result, can be accomplished by one skilled in the art using routine pharmacological methods (see e.g., Fingl et al. 1975, in "The Pharmacological Basis of Therapeutics", which is hereby incorporated herein by reference in its entirety, with particular reference to Ch. 1, p. 1). Typically, human clinical applications of products are commenced at lower dosage levels, with dosage level being increased until the desired effect is achieved.

Dosage amount and interval may be adjusted individually to provide plasma levels of the active moiety, which are sufficient to maintain the antibiotic effects, or minimal effective concentration (MEC). The MEC may vary for each compostion or kit but can be estimated from in vitro data. Dosages necessary to achieve the MEC will depend on individual characteristics and route of administration. However, HPLC assays or bioassays can be used to determine plasma concentrations of released NO. In cases of local administration or selective uptake, the effective local concentration of the drug may not be related to plasma concentration.

The dosage and frequency of administration may be dependent on the subject being treated, on the subject's weight, the severity of the disease, the manner of administration and the judgment of the prescribing physician.

All references cited herein are incorporated herein by reference in their entireties.

EXAMPLES

Example 1

Fabrication of NO-Releasing Particles

NO-releasing microparticle with proven efficacy against multiple strains of planktonic bacteria was previously reported in *Int Forum Allergy Rhinol.* 2018; 8(10):1190-1198. The procedure therein for the preparation of SNO-MP is incorporated by reference. In brief, an organosilica sol-gel monolith was formed containing many covalently attached nitrosated thiol groups. Hydrolyzed tetramethyl orthosilicate (TMOS) or tetraethyl orthosilicate (TEOS), hydrolyzed/nitrosated mercaptopropyl-trimethoxysilane (MPTS), polyethylene glycol, and sodium phosphate were mixed and maintained at room temperature to form a spanning network of siloxane (Si—O—Si) linkages through condensation. The resultant porous sol-gel monolith was lyophilized, dry milled, and then pestled to a micron-sized powder with particle diameters of 5-10 μm. Blank microparticles incapable of NO release (B-MP) were created by performing the aforementioned steps with the exception of nitrosation.

Manuka Honey Formulation Preparation

MH containing a minimum of 0.083 mg/mL methylglyoxal (MGO) (Comvita, New Zealand) was stored at room temperature in the dark prior to use. Stock MH solution was made by dissolving MH in PBS at 37° C. on a rotator to make a 14% wt/vol MH solution for a final minimum MGO concentration of 0.012 mg/mL.

Measurement of NO Release Rate

NO release rates were measured using a Sievers 280i nitric oxide analyzer (GE Instruments, Boulder, CO). Samples were dispersed in 5 mL tryptic soy broth (TSB) or MH 14% w/v in TSB at room temperature. Release kinetics were analyzed using Sievers NOAnalysis software (GE Instruments) with 12 measurements per minute recorded for 280 total minutes.

Titration of Nitrite Dose

To determine the optimal concentration of nitrite to use in subsequent biofilm experiments, the efficacy of serial dilutions of nitrite, in combination with a fixed concentration of MH was evaluated, using a colony forming unit (CFU) assay. An overnight-grown culture of the PA1 strain in TSB was diluted to $10^8$ cells/mL based on McFarland equivalence turbidity standard No. 0.5 (Thermo Fisher Scientific) and then adjusted to $10^5$ cells/mL in TSB. Suspensions were treated with MH, nitrite, and serial dilutions of nitrite from 10 mM to 1 μM combined with MH. Untreated bacteria were used as negative controls. Bacterial suspensions were mixed using a tube rotator to ensure uniform distribution of bacteria and then incubated at 37° C. for 6 hours. Suspensions were then diluted in PBS and plated on TSA. Bacterial viability was determined by counting the number of colonies established on an agar plate after overnight incubation at 37° C.

Biofilm Preparation

A culture of PA, grown overnight in TSB, was diluted to $10^8$ cells/mL. The bacterial suspension was then adjusted to $10^5$ cells/mL in TSB and inoculated into an 8 well LabTek II Chambered #15 Coverglass System (Thermo Fisher Scientific). The chamber system was incubated at 37° C. for 48 hours. The media was replenished after 24 hours to maintain bacterial viability.

Evaluation of Manuka Honey and Nitrite, alone and combined, on Biofilm Viability Established biofilms were divided into four treatment groups: 1) negative control with untreated bacterial suspension, 2) MH, 3) nitrite (10 mM), and 4) MH administered with nitrite (10 mM). Bacteria were treated with the appropriate treatment solution, as above, for 6 hours under complete darkness at 37° C. followed by washing with PBS. Staining was performed using the BacLight LIVE/DEAD Bacterial Viability kit (Invitrogen, Carlsbad, CA). The LIVE/DEAD kit solution constituting Syto9 and propidium iodide was then applied to each well of the chamber slide system for 1 hour at room temperature in darkness. After incubation, each sample was rinsed with PBS and incubated in 10% buffered formalin for 20 minutes at room temperature in darkness. Afterwards, samples were washed with PBS for evaluation with a confocal laser scanning microscope (CLSM). This experiment was repeated in triplicate for both the PA1 and ATCC 15692 strains.

Evaluation of manuka honey with nitrite platform combined with NO-releasing microparticles on biofilm viability Established biofilms were divided into multiple treatment groups: 1) negative control with untreated bacterial suspension, 2) B-MP (10 mg/mL), 3) SNO-MP (10 mg/mL), 4) MH with SNO-MP (10 mg/mL), 5) MH with nitrite (10 mM), and 6) MH with nitrite (10 mM) combined with SNO-MP (10 mg/mL). SNO-MP, whether blank or active, was applied at a concentration of 10 mg/mL based on previously published data demonstrating efficacy against planktonic bacteria at this concentration. Biofilms were treated as described above prior to evaluation with CLSM. This experiment was repeated at least twice with the PA1 and ATCC 15692 strains.

Biofilm Quantification

Images of biofilms were taken using a TCS SP5 CLSM (Leica Microsystems, Wetzlar, Germany) configured to a 488-nm argon laser with a 63× objective. Five to 10 image-stacks (Z-stacks) of each individual sample were taken corresponding to the areas of highest biofilm growth. Each Z-stack consisted of 0.5 μm individual sliced images of the same area of tissue. Volocity software (PerkinElmer, Waltham, MA) was used to quantify biofilm viability and biomass in each Z-stack.

Statistical Analysis

Statistical analysis was performed using SPSS version 21.0 (IBM, Armonk, NY). Differences between treatment groups were analyzed using the non-parametric Mann-Whitney U test. Statistical significance was set at p 0.05.

Results

NO Release Kinetics

Figure 1:
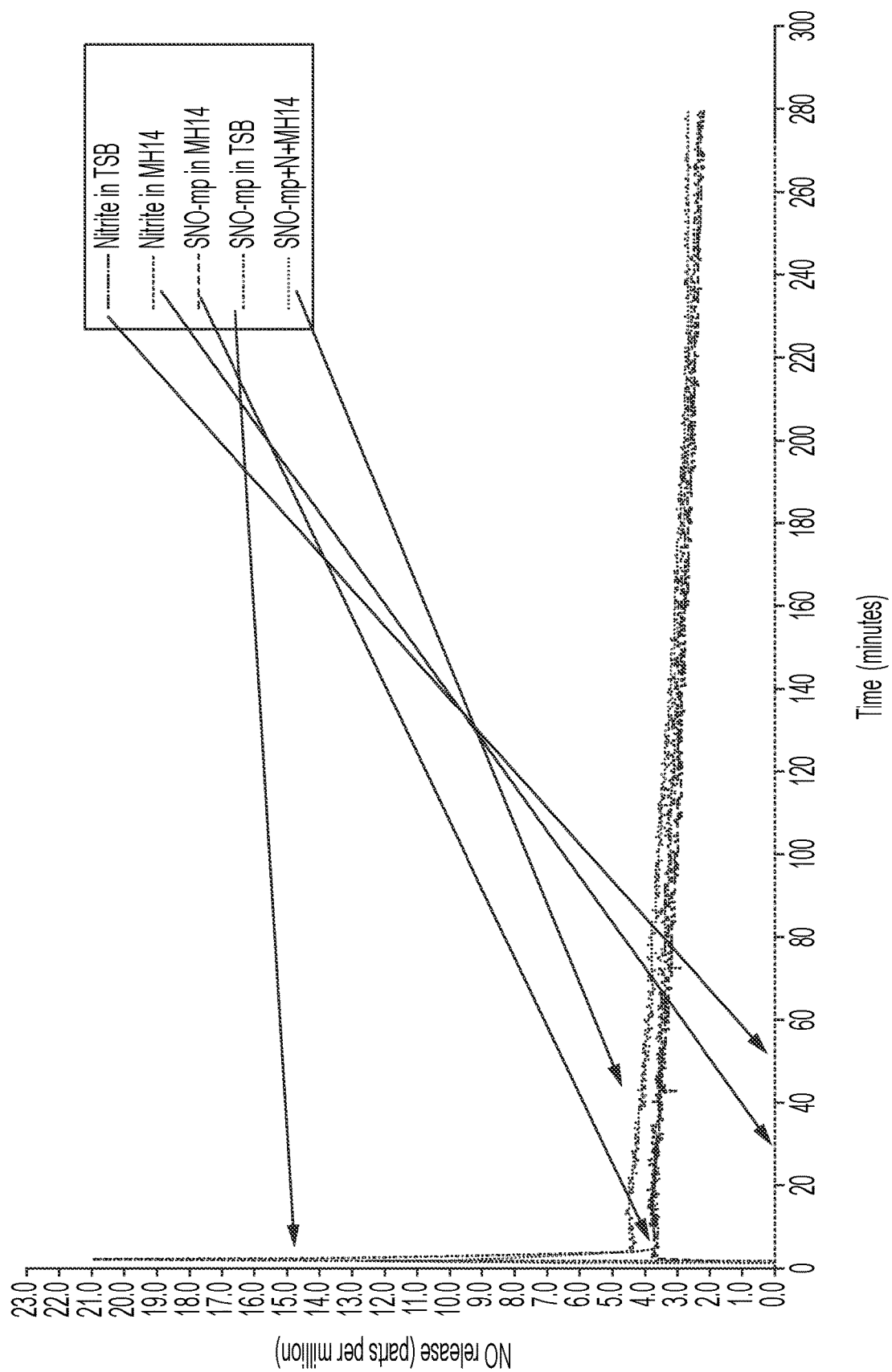
FIG. 1. Nitric oxide (NO) release curves measured using a NO analyzer over the course of 280 minutes at neutral pH in vitro. Treatment groups included: i) nitrite alone in tryptic soy broth, ii) manuka honey (MH) with nitrite, iii) SNO-MP in tryptic soy broth, iv) NO-releasing microparticle (SNO-MP) with MH, v) SNO-MP with nitrite and MH, and vi) blank microparticle (blank-MP) incapable of NO release with nitrite and MH. Nitrite was used at 5 mM concentration; MH at 14% w/v; SNO-MP and blank-MP at 5 mg/mL. Key points are that there is no NO production from just nitrite in TSB. There is also very little NO detected from the nitrite in MH (14%) which is attributed to the long delay subsequent to mixing resulting in loss of NO. The SNO-MP in TBS show a spike followed by slow release. That spike is lost when the SNO-MP are in MH. The addition of nitrite to the SNO-MP/MH mixture restores the spike and enhances the amplitude of the sustained release phase.

An NO analyzer was used to quantify NO release from each formulation in real-time over the course of 300 minutes (FIG. 1). As anticipated, nitrite alone (5 mM) did not release NO with less than 0.1 parts per million (ppm) NO detected (mean 0.004±0.001 ppm [range 0.003-0.009]). MH can reduce nitrite to generate NO at low levels evidenced by the observed linear increase in NO release over the course of 280 minutes (mean 0.020±0.007 ppm [range 0.005-0.034]). The addition of blank microparticles to the combination of manuka honey and nitrite produced a similar linear increase in NO levels (mean 0.016±0.004 ppm [range 0.005-0.022]). SNO-MP was used at a concentration of 5 mg/mL as higher concentrations, when combined with MH, produced gas bubbles resulting in a noisy baseline which precluded accurate NO release measurements. SNO-MP (5 mg/mL) demonstrated a bolus release of NO over the first 5 minutes, peaking at 21.0 ppm at 2.2 minutes, followed by a logarithmic decay to a sustained plateau release phase (mean 3.114±1.064 ppm [range 0.004-21.000]). The addition of MH to SNO-MP (5 mg/mL) appeared to retard the initial bolus release with a peak NO concentration of 3.9 ppm achieved at 15.3 minutes (mean 2.917±0.497 ppm [0.003-3.900]) followed by a logarithmic decay and sustained plateau phase akin to that seen with SNO-MP alone. Combining SNO-MP (5 mg/mL) with MH and nitrite (5 mM) resulted in a maximum NO concentration of 12.5 ppm at 1.5 minutes followed by a gradual decline to a sustained plateau phase. Of note, this final combination was able to sustain higher levels of NO release relative to SNO-MP for approximately 180 minutes.

*Pseudomonas aeruginosa* isolate

A clinical strain of PA derived from a CRS patient and used in prior work evaluating SNO-MP (PA1), as well as a reference PA strain, ATCC 15692, were used in this study. PA1 demonstrated an antimicrobial resistance typical of PA species without an acquired resistance to fluoroquinolones.

Dose Optimization of Nitrite with Manuka Honey

Figure 2:
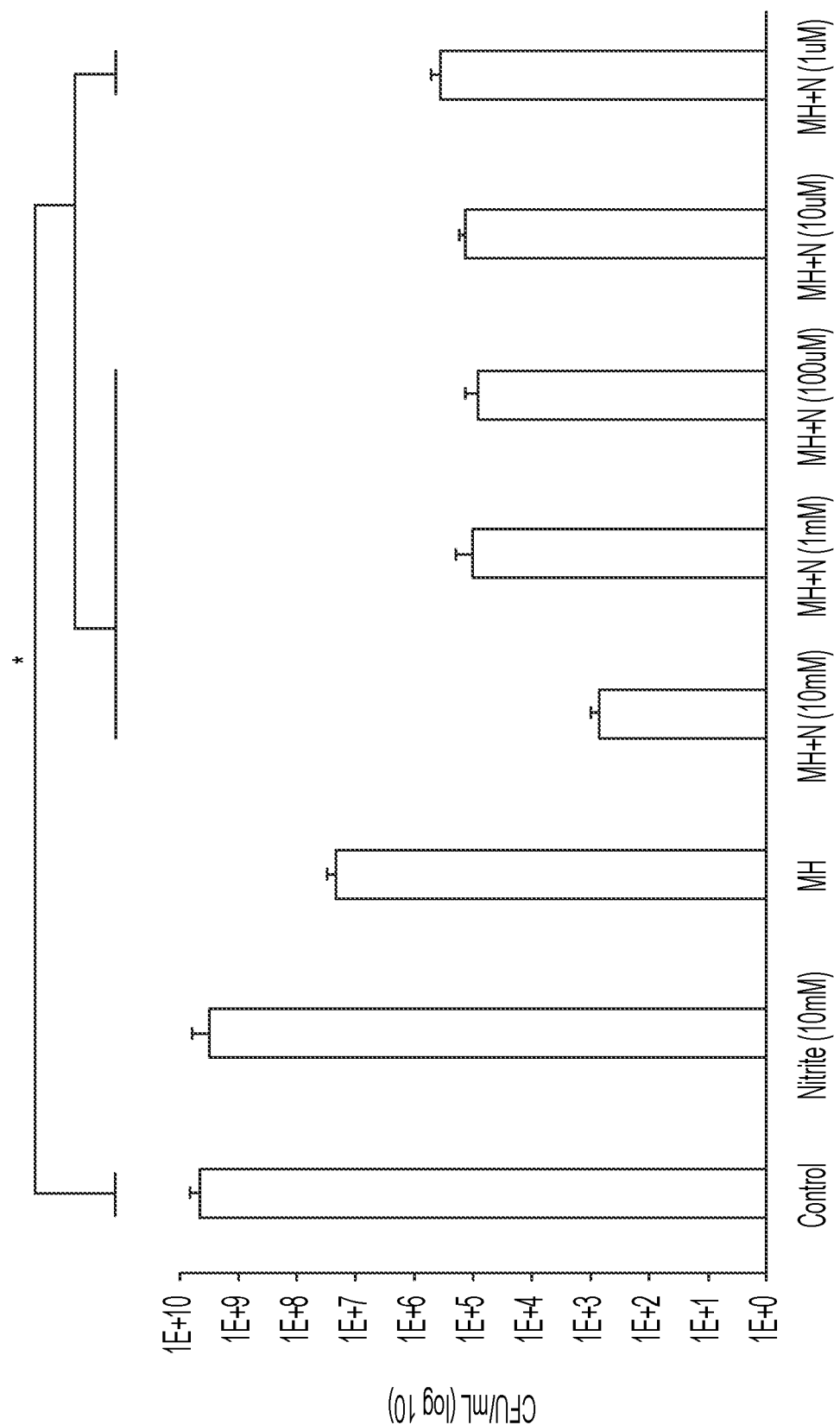
FIG. 2. Colony forming unit assay demonstrating antimicrobial efficacy of nitrite, manuka honey (MH), and MH with serial dilutions of nitrite against *Pseudomonas aeruginosa* planktonic isolates. CFU=colony forming unit; Control=untreated bacteria in tryptic soy broth; N=nitrite. *$p \leq 0.05$ FIG. 3. Ratio of live cells in each treatment group to live cells in the control group after treatment of Pseudomonas aeruginosa biofilm determined by live/dead staining and CLSM in the A) PA1 strain and B) ATCC 15692 strain. Control=untreated bacteria in tryptic soy broth.

As anticipated, nitrite (10 mM) administered alone did not have a significant effect on PA1 CFU (FIG. 2). Monotherapy with MH resulted in a non-significant 2.3 log reduction in CFU versus controls (p=0.083). The addition of nitrite to MH, resulting in the generation of NO, produced a dose-dependent reduction in CFU relative to controls at all concentrations of nitrite (4.1-6.8 log reduction from 1 μM to 10 mM nitrite, respectively, p≤0.05). Given these findings, nitrite (10 mM), alone or in combination with MH, was used for all biofilm experiments.

Efficacy of Manuka Honey and Nitrite against *P. aeruginosa* Biofilms

Figure 3:
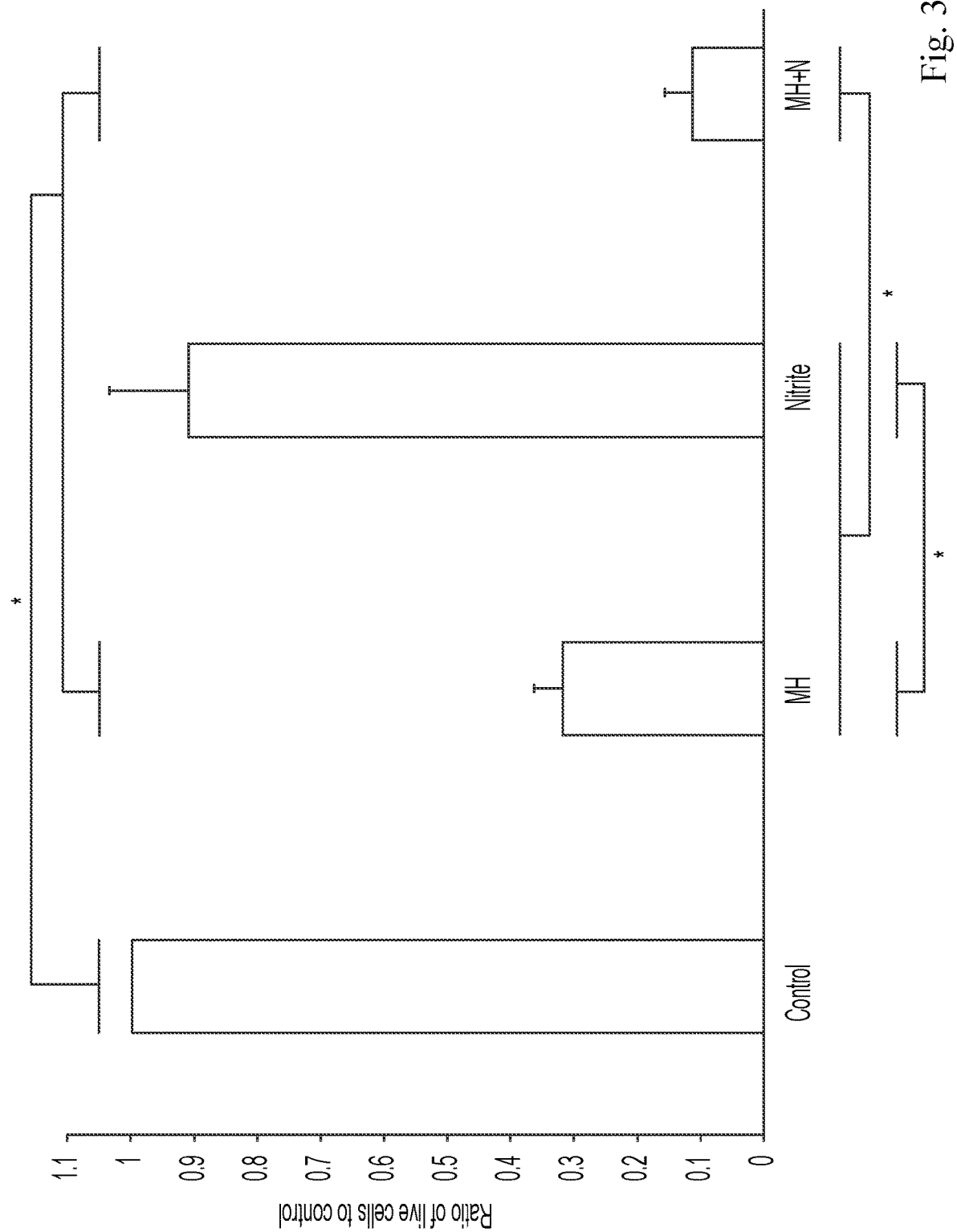

Nitrite, when administered alone, did not significantly reduce biofilm cell viability in either PA strain. In PA1, MH alone demonstrated a significant antibiofilm effect, reducing the number of live cells by 68.2% relative to control (p≤0.0001) (FIG. 3A). The combination of MH and nitrite produced an additional antibiofilm effect with a reduction in cell viability of 88.5%, 87.4%, and 63.9% relative to control, nitrite alone, and MH alone, respectively (p≤0.0001). Treatment of ATCC 15692 with MG reduced live cells by 49.9% relative to control (p≤0.002) (FIG. 3B). MH combined with nitrite produced a reduction in cell viability of 96.9%, 95.7%, and 93.9% relative to control (p≤0.0001), nitrite alone (p≤0.001), and MH alone (p≤0.0001), respectively.

The anti-biofilm efficacy of MH combined with nitrite was demonstrated by a reduction in biofilm volume in PA1 (FIG. 4A, 4B). Relative to control, MH combined with nitrite produced a 95.1% reduction in biofilm volume (p≤0.0001). This represented an improvement over the 85% reduction, relative to control, induced by MH alone (p≤0.0001) or the nonsignificant 43.9% reduction associated with nitrite treatment alone. MH with nitrite produced a 66.4% and 91.3% reduction in volume compared to MH alone (p≤0.001) and nitrite alone (p≤0.0001), respectively. In ATCC 15692, MH alone produced a non-significant 13.0% reduction in biofilm volume relative to control (FIG. 4C, 4D). The combination of MH with nitrite induced a 95.6%, 95.7%, and 95.0% reduction in biofilm volume relative to that in the control (p≤0.0001), nitrite alone (p≤0.002), and MH alone groups (p≤0.0001), respectively.

Combination of Nitric Oxide Generating and Nitric Oxide Releasing Platforms

The current series of experiments demonstrated that SNO-MP has efficacy against PA1 biofilms (FIG. 5A). SNO-MP produced a 61% reduction in cell viability relative to control (p≤0.0001) but, interestingly, this was not significantly better than the 55.2% reduction in viable cells on treatment with blank microparticles incapable of NO release. The addition of MH to SNO-MP resulted in an additive effect producing a 90.0% reduction in live cells compared to controls (p≤0.0001). The most potent antibiofilm treatment in PA1 was the combination of MH and nitrite with SNO-MP. This combination nearly eradicated the biofilm with a 99.76% [log 2.61] reduction in cell viability relative to controls (p≤0.0001), a 99.4% [log 2.2] reduction relative to SNO-MP alone (p≤0.0001), and a 97.6% [log 1.6] reduction relative to MH combined with SNO-MP in the absence of nitrite (p≤0.0001).

Comparatively, studies on ATCC 15692 showed that SNO-MP was even more effective against this strain than against PA1, producing a 98.4% [log 1.8] reduction in cell viability versus control (p≤0.0001) (FIG. 5B). This compares favorably to the 71.3% reduction in live cells produced by blank microparticles relative to control (p≤0.0001). The addition of MH to SNO-MP or MH and nitrite to SNO-MP produced similar 99.2% [log 2.1] and 98.3% [log 1.8] reductions in cell viability, respectively, versus control (p≤0.0001) and were not significant improvements over SNO-MP monotherapy.

The combination of MH with nitrite and SNO-MP was also the most effective intervention in terms of biofilm volume reduction in PA1, producing a 97.7% decrease in volume relative to controls (p≤0.0001) (FIG. 6A, 6B). This result compared favorably to the 95.1% reduction produced by MH with nitrite in the absence of the microparticle (p=0.012) and was superior to the combination of MH and SNO-MP without the presence of nitrite (85.4% reduction in biofilm volume vs. control, p≤0.0001). Importantly, the addition of MH with nitrite to the SNO-MP platform improved on the efficacy of the latter which, alone, produced a 74.7% reduction in biofilm volume. ATCC 15692 biofilm volume was significantly reduced with SNO-MP monotherapy (85.7% vs control, p≤0.0001) (FIG. 6C, 6D). This effect was bolstered by the addition of MH to SNO-MP (97.6% vs control, p≤0.0001) though augmentation of NO release by using MH with nitrite and SNO-MP failed to further reduce biofilm volume (91.4% vs control, p≤0.0001). As with cell viability, SNO-MP, MH with SNO-MP, and MH and nitrite with SNO-MP were statistically comparable in their volume reduction effect.

In this study, it was demonstrated that MH, in combination with nitrite, generates a potent anti-biofilm effect against two strains of PA: ATCC reference 15692 and clinical strain PA1 isolated from a CRS patient. Furthermore, it was found that SNO-MP, previously shown to eradicate planktonic bacterial isolates, is also capable of disrupting PA biofilms, producing a 61% and 75% reduction in the number of viable cells and biofilm volume, respectively, in PA1 and an even more robust 98.4% and 85.7% reduction in viable cells and biofilm volume, respectively, in ATCC 15692. Though a standard has yet to be established in the literature beyond which biofilm killing is considered clinically efficacious, a reduction of 99.9% (3 log) of viable bacteria is considered bactericidal. The combination of SNO-MP with MH and nitrite approaches this threshold in PA1, inducing a 2.6 log reduction in viable cells and a 98% decrease in biofilm volume. ATCC 15692 appeared highly susceptible to the levels of NO produced by SNO-MP with no significant increase in antibiofilm activity achieved through augmentation of NO flux by adding MH or MH and nitrite to SNO-MP. Indeed, SNO-MP containing treatments produced a log 1.8-2.1 reduction in biofilm cell viability and an 85.7-97.6% reduction in biofilm volume. These findings are particularly compelling in the context of PA biofilms which exhibit a 100 to 1000-fold higher minimum bactericidal threshold than planktonic forms.

MH has been shown to induce a 91% reduction in PA biofilms in vitro and has demonstrated efficacy against biofilms in a sheep model of CRS. MH concentrations between 15% and 30% w/v exhibit antibacterial effects. The results confirm that MH is capable of significantly reducing biofilm viability and volume relative to controls. However, PA biofilms treated with MH developed subpopulations of bacteria exhibiting resistance to MH that could be sustained through subsequent generations. In contrast, there has yet to be compelling evidence demonstrating biofilm resistance to NO. The importance of NO in protecting against biofilms is suggested by its role as the end effector of taste receptor activation. Sweet and bitter taste receptors are present on discrete solitary chemosensory cells throughout the upper airway and detect quorum-sensing molecules produced by biofilms leading to the downstream production of NO. More recently, genetic variation in upper airway taste receptor function has been shown to correlate with the severity of CRS in patients. The mechanism of effect of NO is multi-faceted and includes the inactivation of enzymes responsible for bacterial replication, reaction with oxygen to produce toxic species, and binding with superoxide $O2^-$ radicals to form the strong oxidant peroxynitrite.

Though the mean volume of NO produced was approximately 150-fold lower than that released by SNO-MP, the release profile increased in a linear manner over the duration of the measurement period of 280 minutes. This was anticipated as the loss of NO gas into the atmosphere further drives the equilibrium of the reduction reaction towards the right, producing more NO. A similar profile may be seen in vivo where the rapid scavenging of NO may, paradoxically, enhance its production through chemical reduction.

SNO-MP monotherapy demonstrated a potent antibiofilm effect likely related to the large bolus release of NO within minutes of administration followed by a sustained plateau phase. Interestingly, this effect did not appear to be entirely related to NO release as evidenced by the non-significant difference in cell viability and biofilm volume reduction in PA1 relative to blank microparticles incapable of NO release. Interestingly, SNO-MP was significantly more effective than the blank microparticle against the ATCC 15692 strain suggesting that, in some bacterial strains, there may be an added benefit—beyond any intrinsic effect of the microparticles—with nitric oxide release.

It has previously shown that anti-biofilm effects of blank particles postulate a potential deleterious effect of the particle itself on the biofilm lifecycle. This effect may be mediated by thiol groups in the blank microparticle, which harbor intrinsic antioxidant and antimicrobial properties. This has been demonstrated in N-acetylcysteine, a well-characterized molecule that, like our blank microparticle, contains thiol groups. Thiols can irreversibly react with the disulfide bonds of key bacterial proteins involved in growth. The thiol groups can also react with proteins governing the production of extracellular polysaccharide preventing the production of the biofilm extracellular matrix and impairing the adhesion of biofilms to surfaces, thereby interrupting the biofilm lifecycle.

Interestingly, the combination of MH with SNO-MP, and without nitrite, impeded NO release relative to the SNO-MP particle alone. This reduction in NO release may be related to the viscosity of MH which not only affects viscosity of the media in which the microparticles dissolve but, by penetrating the matrix of the microparticle, affects the internal viscosity of the particle as well. As internal viscosity increases, the NO dissociating from the microparticle has a higher probability of recombining with the thiyl radical to reform nitrosothiol rather than escaping into the surrounding media in a process termed geminate recombination. Nevertheless, the reduction in NO release did not appear to negatively impact the anti-biofilm effect.

Combining MH with nitrite and SNO-MP induced the most potent anti-biofilm effect in PA1. NO release from SNO-MP was, again, compromised by a likely viscosity-related mechanism. However, the addition of MH with nitrite had the benefit of sustaining NO release at a higher level during the plateau phase than was observed with SNO-MP alone. This additional NO during the plateau phase cannot be attributed solely to the addition of NO production by MH-mediated nitrite reduction to that released by SNO-MP as the magnitude of the increase was greater than expected. It is hypothesized that the NO generated by the reduction of nitrite re-nitrosated the thiyl radicals in the microparticle, refreshing the nitrosothiol groups, and allowing for a boost in NO release from SNO-MP.

Example 2

MH and 30 mg NAC were mixed well and coated on three soft silicone strips having tiny holes. Separately, PEG 400 (100 uL) and nitrile (10 mg) were mixed well and coated on two solfe silicone strips with tinyl holes. The strips were dried on lyophilizer for about two hours. The strips were layered (NAC layer and nitrite layer alternate positioned) and wrapped into a pocket with parafilm with wholes and tied that pocket to a small rod and inserted in NO analyzer flask and ran for few minutes without water. Then 5 ml water added and NO release monitored for about 7 hours. As shown in FIG. 7, extended release NO was observed.

Example 3

The effect from pH value and amount of water source on the generation of NO was examined. Three NO generation mixtures were prepared. (1) Monuka honey (1 g) was mixed with 200 micromoles of sodium nitrite and 4 ml of water (unbuffered) or PBS (buffered) was added. This mixture was analyzed on a chemiluminsescent nitric oxide analyzer (Siever). (2) Monuka honey (1 g) was mixed with 200 micromoles of sodium nitrite and 240 micromoles of N-acetyl cysteine (Nac) to make Nac-SNO. Four ml of water or PBS was added and this mixture was analyzed on nitric oxide analyzer. (3) Monuka honey (1 g) was mixed with 200 micromoles of sodium nitrite and 50 mg of Nac-SNO-nanoparticles (50 micromoles of Nac-SNO). Four ml of water or PBS was added and this mixture was analyzed on nitric oxide analyzer. FIGS. 8($a$) and 8($b$) show the generation of NO in water and PBS respectively, where NO is generated and released from honey plus nitrite mixtures when mixed (1:4, wt:vol) with either distilled water or PBS. Buffering at a higher pH limited NO production. The presence of NAC or NAC-SNO nanoparticles enhanced the amount of NO released over a sustained time period.

The above mixtures, without water or PBS, were applied to a kimwipe and held above the surface of water in NO analyzer flask and analyzed for NO release. The results were shown in FIG. 8($c$). NO release of the undiluted (no added water or PBS) honey plus nitrite plus NAC or NAC-SNO nps when exposed to moisture increases with time and is sustained.

Example 4

The study on loss of biofilm volume (Pseudomonas a.) as a function of treatment is illustrated in FIG. 9. The tested mixtures in dude: TSB (growth broth/control), MH (Manuka honey 14% diluted in TSB), MH+N (14% MH+sodium nitrite at 10 mM), MH(14%)+NAC (1.622 mg/ml), MH(14%)+nitrite (10 mM)+NAC (1.622 mg/ml), MH (14%)+NACSNO nanoparticles (10 mg/ml), MH+nitrite (10 mM)+NACSNO nanoparticles (10 mg/ml).

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of the drug combiantion, or a step of the method, and may result from a different combination of described consituents, or that other un-described alternate embodiments may be available for a composition, kit or method, is not to be considered a disclaimer of those alternate embodiments. It will be appreciated that many of those un-described embodiments are within the literal scope of the following claims, and others are equivalent.

The invention claimed is:

1. A method of treating a disease or condition selected from an inflammatory skin condition and/or formation of biofilm associated with bacterial growth, comprising administering to a subject in need thereof an effective amount of a composition comprising and anhydrous mixture of: (a) a hygroscopic gelling agent comprising honey and (b) a nitrite source;
wherein the nitrite source is entrapped within the gelling agent,
wherein the composition releases a therapeutically effective amount of nitric oxide (NO) after being exposed to a sufficient amount of water.

2. The method of claim 1, wherein the gelling agent further comprises polyethylene glycol (PEG) for adjusting the viscosity of the gelling agent.

3. The method of claim 1, wherein the composition further comprises a source of S-nitrosothiol groups admixed with the nitrite source.

4. The method of claim 3, wherein the source of the S-nitrosothiol groups is nanoparticles covalently attached to the S-nitrosothiol groups.

5. The method of claim 3, wherein the source of the S-nitrosothiol groups is releasable molecules containing the S-nitrosothiol groups and attached to or enclosed by nanoparticles.

6. The method of claim 5, wherein the releasable molecules are selected from the group consisting of S-nitroso-Glutathione (GSNO), S-nitroso-N-acetylcysteine (SNAC), S-Nitroso-N-acetylpenicillamine (SNAP), and S-nitroso-human serum albumin (SNO-HAS).

7. The method of claim 3, wherein the source of S-nitrosothiol groups is S-nitrosothiol group-containing molecules.

8. The method of claim 3, wherein the amount of the source of S-nitrosothiol groups is selected to provide an extended release of NO.

9. The method of claim 1, wherein the composition further comprises a thiol source.

10. The method of claim 1, wherein the composition is configured to provide an extended release of NO over a period of at least 8 hours.

11. The method of claim 1, wherein the disease or condition is an inflammatory skin condition.

12. The method of claim 1, wherein the disease or condition is formation of biofilm associate with bacterial growth.

13. The method of claim 1, wherein the composition is infused into urinary catheter or into bladder of the subject.

14. The method of claim 1, wherein the composition is administered topically to the subject.

15. The method of claim 1, wherein the ratio between the weight of the gelling agent and the weight of nitrite source ranges from about 50:1 to about 1000:1.

16. The method of claim 1, wherein the gelling agent has a viscosity ranging from about 5000 to about 15,000 centipoise.

17. The method of claim 1, the nitrite source is potassium nitrite, sodium nitrite, rubidium nitrite, strontium nitrite, barium nitrite, calcium nitrite, copper nitrite, zinc nitrite, or mixtures thereof.

18. The method of claim 1, wherein the composition is substantially free from water prior to being administered to the subject.

19. The method of claim 8, wherein the source of the thiol group is nanoparticles having the thiol groups covalently attached thereto or releasable molecules containing the thiol groups.

* * * * *